US005721346A

United States Patent [19]

Lazarevski et al.

[11] Patent Number: 5,721,346
[45] Date of Patent: Feb. 24, 1998

[54] COMPOUNDS OF THE SECOMACROLIDE AND SECOAZALIDE CLASS AND A PROCESS FOR THE PREPARATION THEREOF

[75] Inventors: Gorjana Lazarevski; Gabrijela Kobrehel, both of Zagreb, Croatia

[73] Assignee: PLIVA, farmaceutska, kemijska, prehrambena i kozmetička industrija, dioničko društvo, Zagreb, Croatia

[21] Appl. No.: 611,781

[22] Filed: Mar. 7, 1996

[30] Foreign Application Priority Data

Mar. 27, 1995 [HR] Croatia ................ P950145A

[51] Int. Cl.$^6$ ................ C07H 1/00; C07H 17/00

[52] U.S. Cl. ................ 536/17.9; 536/4.1; 536/7.4; 536/17.2; 536/18.5

[58] Field of Search ................ 536/7.5, 4.1, 18.5, 536/17.2, 17.9

[56] References Cited

U.S. PATENT DOCUMENTS 5,210,235 5/1993 Waddell et al. ................ 549/415

*Primary Examiner*—Elli Peselev
*Attorney, Agent, or Firm*—Pollock, Vande Sande & Priddy

[57] ABSTRACT

The present invention refers to the new compounds of the secomacrolide and secoazalide class, a process for the preparation thereof as well as to new intermediates for the preparation of these seco derivatives.

45 Claims, No Drawings

COMPOUNDS OF THE SECOMACROLIDE AND SECOAZALIDE CLASS AND A PROCESS FOR THE PREPARATION THEREOF

TECHNICAL FIELD

International Patent Classification: A 61 K 31/70, C 07 H 17/08

TECHNICAL PROBLEM

The present invention relates to new compounds of the secomacrolide and secoazalide class, potential intermediates in the preparation of the new macrolide and azalide antibiotics, as well as to a process for the preparation thereof.

PRIOR ART

Erythromycin A is a valuable macrolide antibiotic, whose structure is characterized by 14-member lactone ring having a keto group at C-9 position (McGuire, Antibiot. Chemother., 1952, 2:281). For more than 40 years erythromycin A has been considered to be a safe and active antimicrobial agent for treating gram-positive infections. The principal disadvantages of the use of erythromycin A in human medicine are its restricted range of action against gram-negative bacterial strains; its gastric intolerance with many patients and its loss of activity in an acidic medium with the formation of the inactive metabolite anhydroerythromycin. The spirocyclization of the aglycone ring of erythromycin A is successfully inhibited by chemical transformation of C-9 ketone or of hydroxyl groups at C-6 and/or C-12 position. Thus e.g. by oximation of C-9 ketone with hydroxylamine hydrochloride, followed by Beckmann's rearrangement of the obtained 9(E)-erythromycin A oxime and the reduction of the thus formed bicyclic 6,9-imino ether, there was obtained 9-deoxo-9a-aza-9a-homoerythromycin A, the first macrolide having a 15-membered azalactone ring (Kobrehel G. et al., U.S. Pat. No. 4,328,334, May 1982). By reductive methylation of 9a-amino group according to Eschweiler-Clark process, 9-deoxo-9a-methyl-9a-aza-9a-homoerythromycin A (AZITHROMYCIN) (Kobrehel G. et al., BE Pat. 892 357, July 1982), a prototype of new antibiotics of azalide class was synthesized. In addition to the broad antimicrobial range including gram-negative bacteria and intracellular microorganisms, azithyromycin is also characterized by a specific transport mechanism to the site of application, a long biological half-lite and a short therapy period.

Recently, the hydrolysis and alcoholysis of C-1 lactone of erythromycin A and B, whereby corresponding linear seco-acids or esters are formed (Martin S. F., J. Am. Chem. Soc., 1991, 113, 5478–5480), were described. Further, base catalyzed transformations, which lead to an opening of the macrocyclic ring under the formation of C-1 carboxylate (Waddel S. T. and Blizzard T. A., WO 94/15617, July 1994) were described. There has also been described the formation of new macrolide and azalide rings via a combination of the east 8a-aza-(C-1/C-8) and 9a-aza-(C-1/C-9) fragments of 9-deoxo-8a-aza-8a-homoerythromycin A as well as 9-deoxo-9a-aza-9a-homoerythromycin A with different fragments, which become the west molecule part. It should be emphasized that the above-mentioned obtained C-1/C-9 linear fragment differs from the corresponding azythromycin fragment with regard to the additional ethylene group at C-9 carbon atom.

TECHNICAL SOLUTION

According to our knowledge of the prior art, there have not yet been described linear 9a-azalide fragments of macrolide antibiotics of azalide class of the general formula (I)

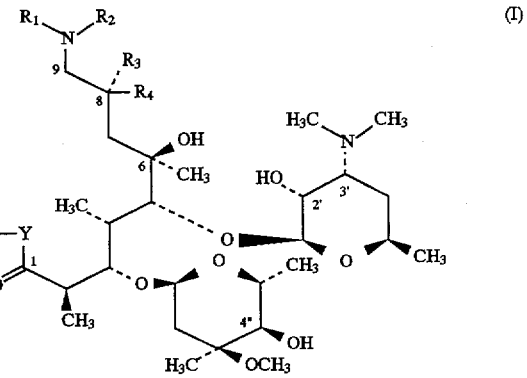

wherein $R_1$ and $R_2$ are the same and represent H or $CH_3$, $R_3$ and $R_4$ are different and represent H or $CH_3$, Y is O or NH, and Z is $CH_3$ or the $CH(CH_3)CH(OH)COH(CH_3)CH(OH)$ $C_2H_5$ group, or their pharmaceutically acceptable addition salts with inorganic or organic acids. The substituents $R_3$ and $R_4$ characterize two epimere forms of the said compound of general formula (I), which only differ structurally in the configuration of the chiral centre at C-8 carbon. Even though the stereochemistry at C-8 carbon has not been established, to the compounds, wherein $R_3$ represents the $CH_3$ group, (R)-configuration is attributed on the basis of similarity of the chemical shifts of these pounds and of the starting 6,9-amino other having C-8(R) configuration.

The present invention also relates to a process and to hitherto not described intermediates for the preparation of the compounds of the general formula (I). The structure of the intermediates is represented by the general formula (II),

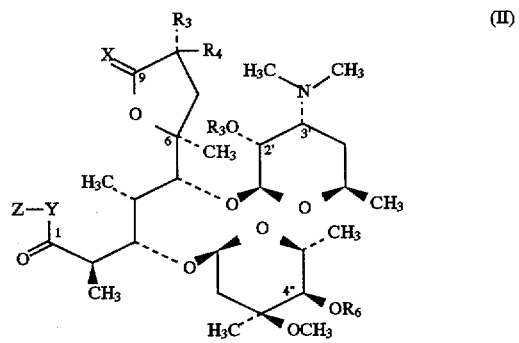

wherein

X is O or $NOR_7$, wherein $R_7$ is H, acyl or arylsulfonyl group, $R_3$ and $R_4$ are different and represent H or $CF_3$, $R_5$ and $R_6$ are the same or different and represent H or acyl group, Y is O or NH and Z is $CH_3$, a $CH(C_2H_5)COH(CH_3)CH(OR_8)CH(CH_3)$ $NHR_9$ or $CH(CH_3)CH(OR_{10})COH(CH_3)CH(OR_{11})$ $C_2H_5$ group, $R_8$ is H or acyl group, and $R_9$ is H, acylsulfonyl group, and $R_{10}$ and $R_{11}$ are the same and represent H or acyl group.

The invention also relates to pharmaceutically acceptable addition salts thereof with inorganic or organic acids.

Generally it can be said that at the new compounds of the general formulas (I) and (II), the "east" part of the molecule including both sugars is structurally identical to the corresponding C-1/C-9 fragment of the macrolactone ring of erythromycin A 6,9-imino ether or of 9-deoxo-9a-aza-9a-homoerythromycin A, whereas the "west" part represents C-1 methylester group or unsubstituted or substituted C-10/C-15 fragment of the starting imino ether with terminal unsubstituted or substituted primary group, or represents the same fragment inversively bound to C-1 atom, yielding, instead of C-1 lactone, new, hitherto not yet described C-1 amides.

Compounds according to general formula (I) of the present invention can be reacted to provide the corresponding azalide compounds using standard reactions, such as described in the literature including J. March, Advanced Organic Chemistry, Reactions, Mechanisms and Structure, J. Wiley & Sons, Inc., III ed., 1985, pp. 366–368, disclosure of which is incorporated herein by reference.

Since the azalide compounds obtainable from compounds according to general formula (I) will have the same "eastern side" of the molecule as the azalides described in WO 94/15617 but will differ in the "western side," it will be apparent to persons skilled in the art that the azalide compounds obtainable from intermediates according to the present invention will exhibit antibacterial action.

For example, from WO 94/15617, it is evident that numerous modifications in the "western side" of the molecule did not cause a decrease of the biological activity of the compounds, therefore, it can be concluded that this part of the molecule is not decisive for the antimicrobic properties.

As stated above, azalide compounds obtainable from intermediates according to the present invention differ just in this "western side" of the molecule, which is unimportant for its antibacterial action. Therefore, the present invention can be used by those skilled in the art without undue experimentation. The disclosure of WO 94/15617 is incorporated herein by reference.

However, the azalide compounds of WO 94/15617 are obtained from essentially different intermediates and by the use of a different type of chemical reactions than those of the present invention, therefore between the present application and WO 94/15617 there exists an essential difference in intermediates, as well as in chemical processes for obtaining the corresponding azalide compounds.

New 9a-azalide fragments of the general formula (I)

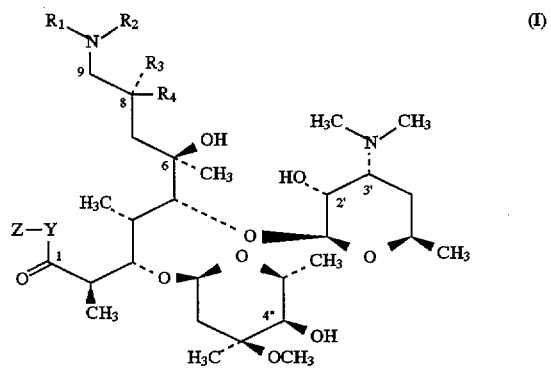

wherein
$R_1$ and $R_2$ are the same and represent H or $CH_3$,
$R_3$ and $R_4$ are different and represent H or $CH_3$,
Y is O or NH, and
Z is $CH_3$ or $CH(CH_3)CH(OH)COH(CH_3)CH(OH)C_2H_5$ group, and their pharmaceutically acceptable addition salts with inorganic or organic acids are obtained by a process, wherein the starting erythromycin A 6,9-imino ether of the formula (III),

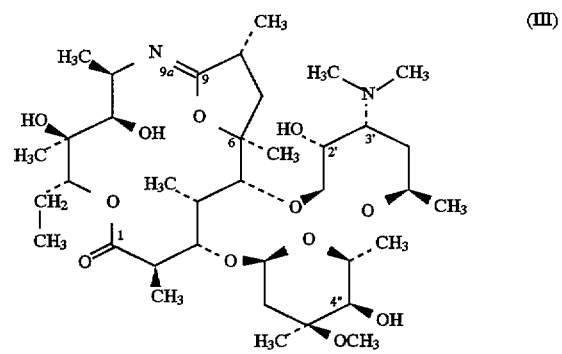

is subjected

A) to the action of an acid under the conditions of the hydrolysis of the imino group and then, if appropriate, to N- and/or O-acylation with acid anhydrides or chlorides and then, if appropriate, to solvolysis, or B) to the reaction with hydroxylamine hydrochloride in the presence of appropriate inorganic or organic bases in one or two reaction steps and then, if appropriate, B1) to the action of appropriate inorganic or organic acids under the conditions of the hydrolysis of the hydroxyimino group and then, if appropriate, to N- and/or O-acylation and then to solvolysis as described under A) or, if appropriate, B2) to N- and/or O-acylation with acid anhydrides and chlorides and then, if appropriate, to solvolysis or, if appropriate, B3) to the action of appropriate organic or inorganic bases under the conditions of internal amine acylation and then, if appropriate, to N- and/or O-acylation with acid anhydrides or chlorides and then, if appropriate, to solvolysis, yielding compounds of the general formula (II),

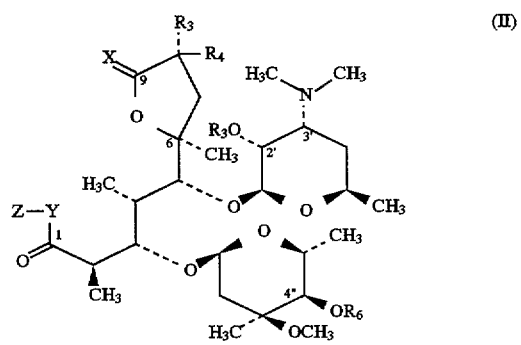

wherein
X is O or $NOR_7$, wherein $R_7$ is H, acyl or arylsulfonyl group,
$R_3$ and $R_4$ are different and represent H or $CH_3$,
$R_5$ and $R_6$ are the same or different and represent H or acyl group,
Y is O or NH, and
Z is $CH_3$, $CH(C_2H_5)COH(CH_3)CH(OR_8)CH(CH_3)NHR_9$ or $CH(CH_3)CH(OR_{10})COH(CH_3)CH(OR_{11})C_2H_5$ group,
$R_8$ is H or acyl group, $R_9$ is H, acyl or arylsulfonyl group, and $R_{10}$ and $R_{11}$ are the same and represent H or acyl group, and their pharmaceutically acceptable addition salts with inorganic or organic acids, which, if appropriate, are subjected to catalytic reduction and then, if appropriate, to reductive N-alkylation with appropriate alkylation agents in the presence of appropriate reductive agents, yielding compounds of the general formula (I), wherein $R_1$, $R_2$, $R_3$, $R_4$, Y and Z have the above-mentioned meanings. The preparation of the new compounds of the general formula (I) and (II) can be represented by reaction schemes 1 and 2.

The compound of the general formula (II), wherein X and Y are the same and represent O, $R_3$ is $CH_3$ and $R_4$ is H, $R_5$ and $R_6$ are the same and represent H, Z is $CH(C_2H_5)COH(CH_3)CH(OR_8)CH(CH_3)NHR_9$, wherein $R_8$ and $R_9$ are the same and represent H (Scheme 1, 2a) is obtained according to the method A) by the action of an acid, preferably glacial acetic acid, upon erythromycin A 6,9-imino ether of formula (III) under the conditions of imine hydrolysis at room temperature within 3 days, whereby C-9/9a-N bond is cleaved, or by the action of inorganic or organic acids under the conditions of hydrolysis of hydroxyimino group upon the compound of the general formula (II) obtained according to the method B), wherein X is $NOR_7$, wherein $R_7$ is H, $R_3$ is $CH_3$ and $R_4$ is H, $R_5$ and $R_6$ are the same and represent H, Y is O and Z is $CH(C_2H_5)COH(CH_3)CH(OR_8)CH(CH_3)NHR_9$, wherein $R_8$ and $R_9$ are the same and represent H. Preferably, the hydrolysis of hydroxyimino group is performed by standing in a mixture of methanol/HCl at room temperature for 10 days. The obtained product having the new 5-membered lactone ring is isolated by means of a common gradient extraction process (pH 5.5, 6.5 and 8.3) followed by the evaporation of the combined organic extracts at pH 8.3 and is subsequently, if appropriate, subjected to N- and/or O-acylation with acid anhydrides or chlorides.

The acylation reaction of the obtained lactone with an acid anhydride is performed by a common process (Jones et al., J. Med. Chem., 1971, 5:631 and Banaszek et al., Rocy. Chem., 1969, 43:763), yielding the corresponding tetraalkanoyl derivatives. Thus e.g. by acylation with acetic acid anhydride in solvent inert to the reaction, preferably in pyridine, at room temperature within 7 days, 2',4",11-O,10-N-tetra-acetate of the general formula (II) is obtained, wherein X and Y are the same and represent O, $R_3$ is $CH_3$ and $R_4$ is H, $R_5$ and $R_6$ are the same and represent $COCH_3$, Z is $CH(C_2H_5)COH(CH_3)CH(OR_8)CH(CH_3)NHR_9$, wherein $R_8$ and $R_9$ are the same and represent $COCH_3$ (Compound 2b). By standing 2',4",11-O,10-N-tetra-acetate in methanol at room temperature within 3 days and solvolysis of the ester group in 2'-position, 4",11-O,10-N-triacetate of the general formula (II) is formed, wherein $R_5$ is H and X, Y, Z, $R_3$, $R_4$, $R_6$, $R_8$ and $R_9$ have the meanings mentioned above at tetraacetate (Compound 2c). The acylation with acid chloride, preferably with 4-bromobenzoyl chloride is performed in a solvent inert to the reaction, preferably in diethylether, at a temperature from 0° C. to 5° C. within 3 hours, yielding 10-N-bromobenzoyl derivative of the general formula (II), wherein X and Y are the same and represent O, $R_3$ is $CH_3$ and $R_4$ is H, $R_5$ and $R_6$ are the same and represent H, Z is $CH(C_2H_5)COH(CH_3)CH(OR_8)CH(CH_3)NHR_9$, wherein $R_8$ is H and $R_9$ is 4-bromo-benzoyl group (Compound 2d).

The reaction of erythromycin A 6,9-imino ether of formula (III) with hydroxylamine hydrochloride is performed according to the method B) in a solvent inert to the reaction, in the presence of inorganic or organic bases, in one or two reaction steps at a temperature from 25° to 70° C. By performing the reaction in one step, a cleavage of C-9/9a-N bond under the formation of the hydroxylimino group at C-9 atom and of a primary amino group at C-10 atom occurs, yielding the compound of the general formula (II), wherein X is $NOR_7$, wherein $R_7$ is H, Y is O, $R_3$ is $CH_3$ and $R_4$ is H, $R_5$ and $R_6$ are the same and represent H, and Z is $CH(C_2H_5)COH(CH_3)CH(OR_8)CH(CH_3)NHR_9$ group, wherein $R_8$ and $R_9$ are the same and represent H, as the only product (Scheme 1, 3a). The reaction is performed with a 1.1 to 30 molar excess of hydroxylamine hydrochloride, preferably with a 5.2 molar excess. Typical solvents inert to the reaction are $C_1$–$C_4$ alcohols, preferably methanol. As acid acceptors there may be used inorganic bases such as alkali metal carbonates or hydrogencarbonates, preferably sodium carbonate or potassium carbonate, or organic bases such as pyridine, which at the same time also act as solvents inert to the reaction. The isolation is performed by the use of the common extraction process with organic solvents, preferably chlorinated hydrocarbons, preferably methylenechloride at pH 10. If the reaction is performed in two steps, i.e. in the first reaction step erythromycin A 6,9-imino ether of formula (III) is subjected to the action of an at least 1.3 molar excess of the above described inorganic or organic bases in a solvent inert to the reaction, preferably in $C_1$–$C_4$-alcohols, preferably in methanol, under the reflux stream of the reaction mixture until imino ether disappears (TLC), then the obtained product mixture is isolated by an extraction process, preferably with chlorinated hydrocarbons, preferably with methylenechloride at pH 8 and then in the second step the crude product is subjected to the action of hydroxylamine hydrochloride in the presence of inorganic or organic bases as described above, the reaction is not unambiguous. The obtained product mixture is isolated by gradient extraction with organic solvents, preferably with methylenechloride at pH 8 and 10. By concentrating the combined organic extracts at pH 10, a mixture of two products is obtained, one of which is identical to the compound (3a) and the other is its C-8(S)-enantiomer of the general formula (II), wherein X is $NOR_7$, wherein $R_7$ is H, Y is O, $R_3$ is H and $R_4$ is $CH_3$, $R_5$ and $R_6$ are the same and represent H, and Z is $CH(C_2H_5)COH(CH_3)CH(OR_8)CH(CH_3)NHR_9$ group, wherein $R_8$ and $R_9$ are the same and represent H (Scheme 2, 3b). By evaporating the combined organic extracts at pH 8, in addition to the compounds (3a) and (3b), there are also obtained two isomeric C-8 oximes of the general formula (II), wherein X is $NOR_7$, wherein $R_7$ is H, Y is O, $R_3$ and $R_4$ are different and represent H or $CH_3$ group, $R_5$ and $R_6$ are the same and represent H, and Z is $CH_3$ (Scheme 2, 7a and 7b) as a result of simultaneous cleaving of the C-9/9a-N bond and of the macrocyclic C-1 lactone under the formation of C-1 metoxylate. The obtained compounds (7a) and (7b) are separated by chromatography on silica gel column using a 6:1:0.1 $CHCl_3$:$CH_3OH$:conc. $NH_4OH$ system and then, if appropriate, subjected to catalytic reduction.

Oximes (3a) and (3b) with terminal amino group are subjected, if appropriate, to N- and/or O-acylation with acid anhydrides and chlorides as described in method A) and then, if appropriate, to solvolysis. Thus e.g. by acylation of compound (3a) with acetic acid anhydride, there is obtained 2',4",11-O,10-N-tetraacetyl 9(E)-acetoxime of the general formula (II), wherein X is $NOR_7$, wherein $R_7$ is $COCH_3$ group, $R_3$ is $CH_3$ and $R_4$ is H, $R_5$ and $R_6$ are the same and represent $COCH_3$, Y is O and Z is $CH(C_2H_5)COH(CH_3)CH(OR_8)CH(CH_3)NHR_9$ group, wherein $R_8$ and $R_9$ are the same and represent $COCH_3$ (Compound 3c), which, if appropriate, is subjected to solvolysis, preferably methanolysis, yielding the compound of the general formula (II), wherein X is $NOR_7$, wherein $R_7$ is H, $R_3$ is $CH_3$ and $R_4$ and $R_5$ are the same and represent H, $R_6$ is $COCH_3$, Y is O and Z is $CH(C_2H_5)COH(CH_3)CH(OR_8)CH(CH_3)NHR_9$ group, wherein $R_8$ and $R_9$ are the same and represent $COCH_3$ (Compound 3d). By reacting compounds (3a) and (3b) with acid chlorides in a solvent inert to the reaction in the presence of inorganic or organic bases at a temperature from 0° C. to 25° C. mono- and disubstituted acyl derivatives are obtained, which, if appropriate, are separated by chromatography on silica gel column by the use of 85:15 $CH_2Cl_2:CH_3OH$ solvent system. Preferably, by reacting compound (3a) with tosylchloride in the presence of $NaHCO_3$ in acetone within 3 hours there are obtained compounds of the general formula (II), wherein X is $NOR_7$, wherein $R_7$ is tosyl, $R_3$ is $CH_3$ and $R_4$, $R_5$ and $R_6$ are the same and represent H, Y is O and Z is $CH(C_2H_5)COH(CH_3)CH(OR_8)CH(CH_3)NHR_9$ group, wherein $R_8$ is H and $R_9$ is tosyl (Compound 3e) or wherein X is $NOR_7$, wherein $R_7$ is H, $R_3$ is $CH_3$ and $R_4$, $R_5$ and $R_6$ are the same and represent H, Y is O and Z is $CH(C_2H_5)COH(CH_3)CH(OR_8)CH(CH_3)NHR_9$ group, wherein $R_8$ is H and $R_9$ is tosyl (Compound 3f).

If appropriate, compounds (3a) and (3b) are subjected to the action of bases under the conditions of internal amine acytation and then, if appropriate, to catalytic reduction. The internal acylation reaction of the above primary amines is performed at room temperature in the presence of inorganic and organic bases, preferably ammonium hydroxide, potassium or sodium hydroxide or triethylamine, whereat an internal migration of C-1 acyloxy group from oxygen to the terminal amino group occurs, giving rise to the inversion of C-10/C-15 west molecule fragment and to the formation of C-1 amide of the general formula (II), wherein X is $NOR_7$, wherein $R_7$ is H, $R_3$ and $R_4$ are different and represent H or $CH_3$, $R_5$ and $R_6$ are the same and represent H, Y is NH and Z is $CH(CH_3)CH(OR_{10})COH(CH_3)CH(OR_{11})C_2H_5$ group, wherein $R_{10}$ and $R_{11}$ are the same and represent H (Scheme 2, 4a and 4b), which, if appropriate, are subjeered to N- and/or O-acylation with acid anhydrides or chlorides or, if appropriate, to catalytic reduction.

The reaction of N- and/or O-acylation of compounds (4a) and (4b) with acid anhydrides according to method A) yields 2',4"-O-diacyl-1N-(2,4-O-diacyl)-9(E)acyloxime. Thus e.g. by acylation of compound (4a) with acetic acid anhydride in pyridine at room temperature within 10 days, a compound of the general formula (II) is obtained, wherein X is $NOR_7$, wherein $R_7$ is $COCH_3$ group, $R_3$ is $CH_3$ and $R_4$ is H, $R_5$ and $R_6$ are the same and represent $COCH_3$, Y is NH and Z is $CH(CH_3)CH(OR_{10})COH(CH_3)CH(OR_{11})C_2H_5$ group, wherein $R_{10}$ and $R_{11}$ are the same and represent $COCH_3$ (Compound 4c). If appropriate, the compound (4c) is subjected to solvolysis, preferably methanolysis, whereat a deacylation of 2'-position or of 2'- and 9-oximester group occurs, yielding compounds of the general formula (II), wherein X is $NOR_7$, wherein $R_7$ is $COCH_3$-group, $R_3$ is $CH_3$ and $R_4$ is H, $R_5$ is H, $R_6$ represents $COCH_3$, Y is NH and Z is $CH(CH_3)CH(OR_{10}) COH(CH_3)CH(OR_{11})C_2H_5$ group, wherein $R_{10}$ and $R_{11}$ are the same and represent $COCH_3$ (Compound 4d), or X is $NOR_7$ wherein $R_7$ is H, $R_3$ is $CH_3$ and $R_4$ is H, $R_5$ is H, $R_6$ is $COCH_3$, Y is NH and Z is $CH(CH_3)CH(OR_{10})COH(CH_3)CH(OR_{11})C_2H_5$ group, wherein $R_{10}$ and $R_{11}$ are the same and represent $COCH_3$ (Compound 4e). Analogously to the tosyl derivatives (3e) and (3f) also monosubstituted acyl derivatives are obtained by the reaction with acid chlorides. Preferably, by the reaction of (4a) with tosyl chloride in acetone in the presence of $NaHCO_3$ at room temperature with 12 hours, the tosyl derivative of the general formula (II) is obtained, wherein X is $NOR_7$, wherein $R_7$ is tosyl, $R_3$ is $CH_3$, $R_4$, $R_5$ and $R_6$ represent H, Y is NH and Z is $CH(CH_3)CH(OR_{10})COH(CH_3)CH(OR_{11})C_2H_5$ group, wherein $R_{10}$ and $R_{11}$ are the same and represent H (Compound 4f).

Catalytic reduction of the above stated oximes (4a, 4b, 7a, and 7b) is performed in a solvent inert to the reaction in the presence of noble metals or their oxides as catalysts at room temperature and at a hydrogen pressure from $5 \times 10^5$ to $7 \times 10^6$ Pa from 10 hours to 3 days. Preferably, the reduction is performed in glacial acetic acid by the use of platinum (IV) oxide as a catalyst within 10 hours at a hydrogen pressure of $7 \times 10^6$ Pa, thereafter the product is isolated by the common gradient extraction process (pH 5.5, 9.0 and 10.5) with chlorinated hydrocarbon, preferably chloroform, followed by the evaporation of the combined organic extracts at pH 10.5. The obtained amines of the general formula (I), wherein $R_1$ and $R_2$ are the same and represent H, $R_3$ is $CH_3$, $R_4$ is H, or $R_3$ H and $R_4$ is $CH_3$, Y is O or NH and Z is $CH_3$ or $CH(CH_3)CH(OH)COH(CH_3)CH(OH)C_2H_5$ group (Scheme 2, 5a, 5b, 8a, and 8b), are, if appropriate, subjected to reductive N-alkylation. Preferably, the reductive N-methylation is performed with 1 to 4 equivalents of formaldehyde (37%) in the presence of the same or double quantity of formic acid (98–100%) in a solvent inert to the reaction such as halogenated hydrocarbons, preferably in chloroform at reflux temperature of the reaction mixture within 2 to 20 hours, which depends upon the quantity of the used aldehyde or acid. The obtained product is isolated by the common gradient extraction process (pH 5.0 and 9.5) followed by the evaporation of the combined organic extracts at pH 9.5 and, if appropriate, it is purified by chromatography on a silica gel column by the use of 6:1:0.1 $CHCl_3:CH_3OH$:conc. $NH_4OH$ system yielding dimethylamino derivatives of the general formula (I), wherein $R_1$ and $R_2$ are the same and represent $CH_3$, $R_3$ is $CH_3$ and $R_4$ is H, or $R_3$ is H and $R_4$ is $CH_3$, Y is O or NH and Z is $CH_3$ or $CH(CH_3)CH(OH)COH(CH_3)CH(OH)C_2H_5$ group (Scheme 2, 6a, 6b, 9a, and 9b).

Pharmaceutically acceptable addition salts, which are also an object of the present invention, are obtained by the reaction of seco derivatives of the general formulas (I) and (II) with at least an equimolar amount of appropriate inorganic or organic acids such as hydrochloric acid, hydroiodic acid, sulfuric acid, phosphoric acid, acetic acid, propionic acid, trifluoroacetic acid, maleic acid, citric acid, stearic acid, succinic acid, ethylsuccinic acid, methanesulfonic acid, benzenesulfonic acid, p-toluenesulfonic acid, laurylsufonic acid etc. in a solvent inert the reaction. The addition salts are isolated by filtration if they are insoluble in the solvent inert to the reaction, by the precipitation with a non-solvent or by the evaporation of the solvent, mostly by the lyophilization process.

By performing the reactions according to the aforesaid steps, an opening of the 15-membered azalactone ring of erythromycin A 6,9-imino ether occurs, yielding seco derivatives with different very reactive terminal functional groups, which also makes possible the preparation of a whole series of new macrolides or azalides with modified macrocyclic aglycone. At the compounds with an inversion of the "west" part of the molecule (4, 5 and 6), 2,3,4-trihydroxy-1,3-dimethyl-hexyl group represents the C-10/C-15 fragment of erythromycin A 6,9-imino ether, wherein for the sake of simplicity the position designations of carbon atoms existing prior to the inversion of the fragment have been kept at stating the spectroscopic data. These designations are represented in Schemes 1 and 2.
SCHEME 1
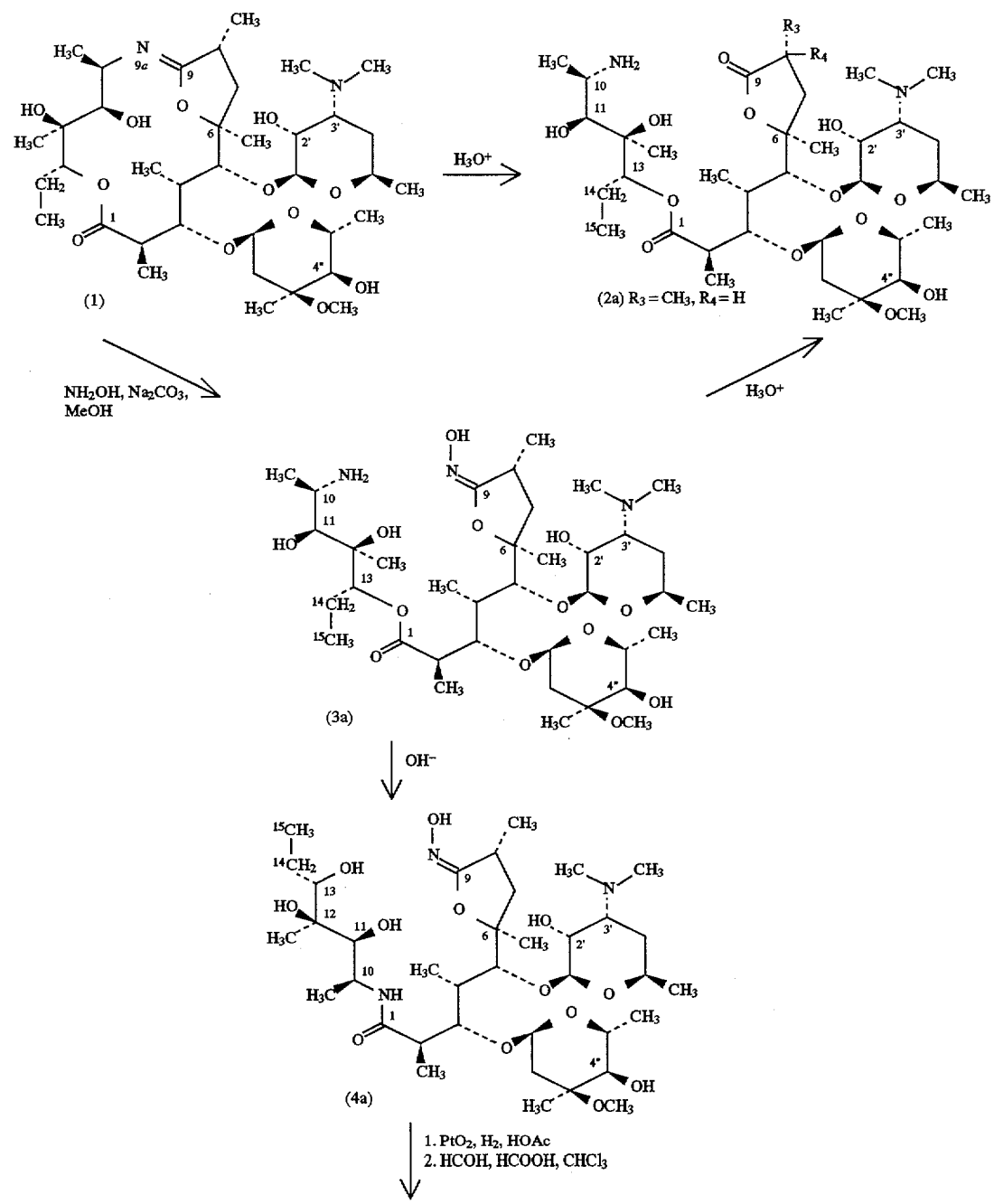

-continued
SCHEME 1
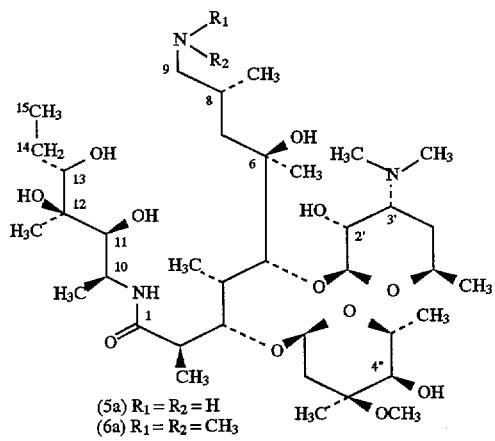
(5a) R₁ = R₂ = H
(6a) R₁ = R₂ = CH₃
SCHEME 2
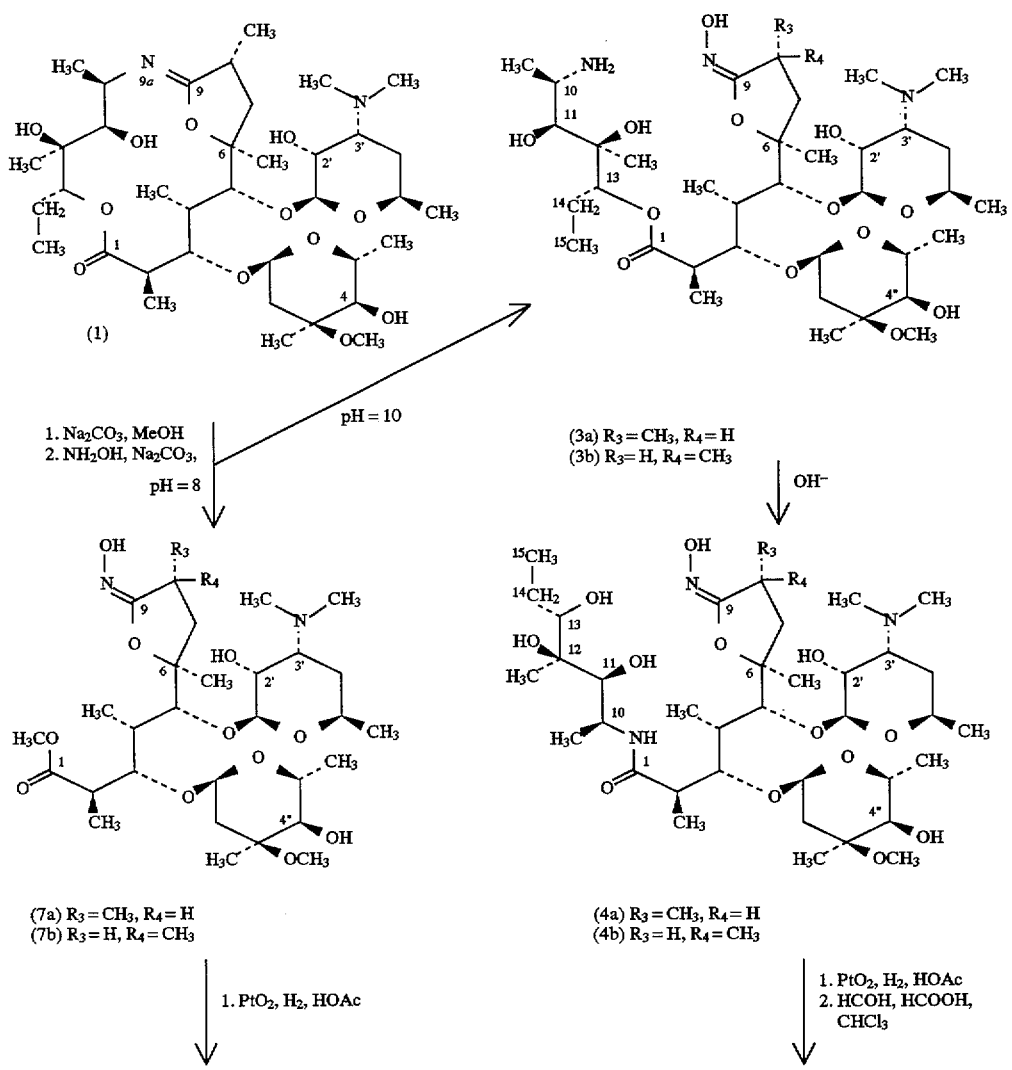

-continued
SCHEME 2

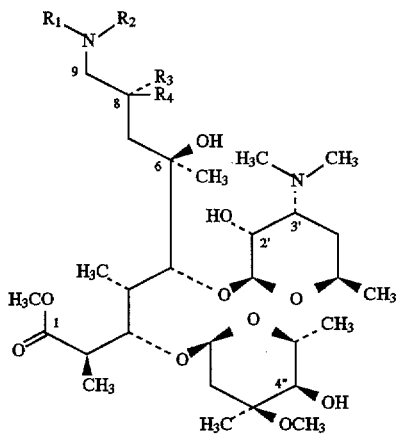
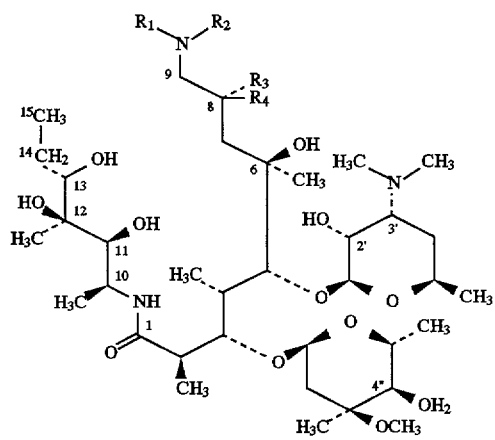

(8a) $R_1 = R_2 = R_4 = H, R_3 = CH_3$
(8b) $R_1 = R_2 = R_3 = H, R_4 = CH_3$
(9a) $R_1 = R_2 = R_3 = CH_3, R_4 = H$
(9b) $R_1 = R_2 = R_4 = CH_3, R_3 = H$ (5a) $R_1 = R_2 = R_4 = H, R_3 = CH_3$
(5b) $R_1 = R_2 = R_3 = H, R_4 = CH_3$
(6a) $R_1 = R_2 = R_3 = CH_3, R_4 = H$
(6b) $R_1 = R_2 = R_4 = CH_3, R_3 = H$

The following examples are intended only to illustrate the present process and not to limit the scope of the invention.

EXAMPLE 1

9-deoxo-6-deoxy-6,9-epoxy-8(R)-methyl-10-amino-9,10-secoerythromycin A 9(E)-oxime (3a)

Method A

To an erythromycin A 6,9-iminoether solution (1) (36.0 g, 0.049 mole) in $CH_3OH$ abs. (750 ml), $NH_2OH \cdot HCl$ (18 g, 0.259 mole) and $Na_2CO_3$ (6.8 g, 0.0642 mole) were added and then the reaction mixture was stirred under reflux for 3 hours. The reaction suspension was evaporated at reduced pressure and to the solid residue 240 ml $H_2O$ and 240 ml $CH_2Cl_2$ (pH 6.8) were added. The pH was adjusted to 10 by the addition of 20% w/v NaOH and the aqueous part was repeatedly extracted with $CH_2Cl_2$. After drying over $K_2CO_3$ the combined organic extracts were evaporated to dryness and the obtained product was dried in high vacuum (6 hours, 40° C.) yielding 34.3 g (91%) of TLC homogeneous substance (3a).

IR ($CHCl_3$) $cm^{-1}$: 3425, 2970, 1720, 1690, 1580, 1455, 1380, 1300, 1260, 1165, 1050. $^1H$ NMR (300 MHz, $CDCl_3$) $\delta$: 4.98 (H-1"), 4.78 (H-13), 4.45 (H-1'), 4.60 (H-3), 3.90 (H-5), 3.49 (H-11), 3.28 (3"-$OCH_3$), 3.05 (H-10), 2.92 (H-8), 2.84 (H-2), 2.28 /3'N($CH_3$)$_2$/, 2.08 (H-7a), 1.88 (H-7b), 1.87 (H-14a), 1.82 (H-4), 1.51 (H-14b), 0.87 (H-15). $^{13}C$ NMR (75 MHz, $CDCl_3$) $\delta$: 175.5 (C-1), 161.1 (C-9), 103.1 (C-1'), 95.0 (C-1"), 88.5 (C-6), 81.9 (C-5), 78.1 (C-13), 76.7 (C-3), 73.5 (C-12), 72.5 (C-11), 48.7 (3"-$OCH_3$), 46.7 (C-10), 43.4 (C-2), 39.8/3'N($CH_3$)$_2$/, 39.7 (C-4), 31.9 (C-8), 21.3 (C-14), 10.6 (C-15). FAB ($MH^+$) 764.4.

Method B

To an erythromycin A 6,9-imino ether solution (1) (36.0 g, 0.049 mole) in pyridine (100 ml), $NH_2OH \cdot HCl$ (18 g, 0.259 mole) was added and then the reaction mixture was stirred for 3 hours at room temperature. To the reaction solution $H_2O$ (400 ml) and $CH_2Cl_2$ (140 ml) were added and the product was isolated by gradient extraction at pH 7.0 and 10.0. By evaporating the combined organic extracts at pH 10.0, 25.0 g (66.4%) of a product (3a) with the identical physical-chemical constants as described at Method A were obtained.

EXAMPLE 2

2',4",11-O,10-N-tetraacetyl-9-deoxo-6-deoxy-6,9-epoxy-8(R)-methyl-10-amino-9,10-secoerythromycin A 9(E)-acetoxime (3c)

To a solution of (3a)(1.0 g, 0.0013 mole) in pyridine (40 ml), acetic acid anhydride (4 ml) was added and then the reaction solution was left to stand for 7 days at room temperature. After completed acetylation (TLC) it was poured into a mixture of water and ice (200 ml) and extracted with $CHCl_3$ at pH 9.0. The combined organic extracts were evaporated at a reduced pressure yielding 1.3 g of a crude product, wherefrom after re-precipitation from an ether-petroleum ether mixture 1.13 g of a TLC homogeneous product (3c) were obtained.

$^1H$ NMR (300 MHz, $CDCl_3$) $\delta$: 6.15 (CONH), 4.97 (H-13), 4.81 (H-2'), 4.78 (H-1"), 4.69 (H-4"), 4.67 (H-11), 4.48 (H-10), 4.59 (H-1'), 4.11 (H-3), 3.79 (H-5), 3.30 (H-3"-$OCH_3$), 3.14 (H-8), 2.75 (H-2), 2.27/3'N($CH_3$)$_2$/, 2.16, 2.13, 2.12, 2.05 and 1.96 ($COCH_3$), 1.90 (H-4), 1.52 (H-14), 0.90 (H-15).

EXAMPLE 3

4",11-O,10-N-triacetyl-9-deoxo-6-deoxy-6,9-epoxy-8(R)-methyl-10-amino-9,10-secoerythromycin A 9(E)-oxime (3d)

A pentaacetate solution (3c) (0.5 g, 0.0005 mole) in methanol (20 ml) was left to stand for 3 days at room temperature. The reaction mixture was evaporated at a reduced pressure and the obtained crude product was purified by chromatography on silica gel column by the use of 90:9:1.5 $CHCl_3$:$CH_3OH$:conc. $NH_4OH$ system yielding 0.250 g of 4",11-O,10-N-triacetate (3d) with the following physical-chemical constants:

$^1H$ NMR (300 MHz, $CDCl_3$) $\delta$: 6.31 (CONH), 4.95 (H-13), 4.85 (H-1"), 4.67 (H-4"), 4.65 (H-11), 4.49 (H-10), 4.49 (H-1'), 4.21 (H-3), 3.79 (H-5), 3.29 (H-3"-OCH$_3$), 3.28 (H-2'), 3.02 (H-8), 2.78 (H-2), 2.30/3'N(CH$_3$)$_2$/, 2.17, 2.13, and 1.96 (COCH$_3$), 2.07 (H-7a), 2.02 (H-4), 1.85 (H-14a), 1.49 (H-14b), 0.88 (H-15). $^{13}$C NMR (75 MHz, CDCl$_3$) δ: 175.0 (C-1), 172.0, 170.7 and 169.3 (COCH$_3$, 162.1 (C-9), 103.5 (C-1'), 95.5 (C-1"), 89.6 (C-6), 81.2 (C-5), 78.3 (C-11), 78.1 (C-3), 76.8 (C-13), 74.9 (C-12), 49.3 (3'-OCH$_3$), 45.0 (C-10), 42.5 (C-2), 40.1/3'N(CH$_3$)$_2$/, 39.5 (C-7), 38.4 (C-4), 32.7 (C-8), 23.1, 20.6 and 20.6 (COCH$_3$), 21.9 (C-14), 10.7 (C-15).

EXAMPLE 4

9-O,10-N-ditosyl-9-deoxo-6-deoxy-6,9-epoxy-8(R)-methyl-10-amino-9,10-secoerythromycin A 9(E)-oxime (3e)

10-N-tosyl-9-deoxo-6-deoxy-6,9-epoxy-8(R)-methyl-10-amino-9,10-secoerythromycin A 9(E)-oxime (3f)

The substance (3a)(2.0 g, 0.0026 mole) from Example 1 was suspended in 70 ml of acetone and cooled to 0°–5° C. To the reaction mixture solutions of tosyl chloride (1.34 g, 0.007 mole) in acetone (30 ml) and NaHCO$_3$ (0.6 g, 0.007 mole) in water (95 ml) were simultaneously added dropwise under stirring within 30 minutes. The reaction suspension was stirred for further 3 hours at room temperature, then acetone was evaporated at a reduced pressure and the aqueous residue was extracted with CHCl$_3$ at pH 5.0. After drying over K$_2$CO$_3$ and evaporation of CHCl$_3$, 2.58 g of product mixture of (3e) and (3f) were obtained. By chromatography of the crude product (1.8 g) on silica gel column by the use of 85:15 CH$_2$Cl$_2$:CH$_3$OH, 0.250 g of TLC pure (CHCl$_3$:CH$_3$OH, 7:3) compound (3e) with Rf 0.63 and 1.1 g of compound (3f) with Rf 0.43 were obtained.

Compound (3e)

IR (CHCl$_3$) cm$^{-1}$: 3460, 2975, 2940, 1730, 1660, 1600, 1455, 1370, 1190, 1180, 1160, 1090, 1050, 1000, 975, 855, 815, 665. $^1$NMR (300 MHz, CDCl$_3$) δ: 7.80 (p-Ph), 7.30 (p-Ph), 4.81 (H-13), 4.78 (H-1"), 4.48 (H-1'), 4.26 (H-3), 3.96 (H-5"), 3.76 (H-5), 3.68 (H-5'), 3.60 (H-11), 3.50 (H-10), 3.41 (H-2'), 3.23 (3"-OCH$_3$), 3.09 (H-8), 3.03 (H-4"), 2.94 (H-2), 2.54/3'N(CH$_3$)$_2$/, 2.43 (p-Ph-CH$_3$), 2.41 (p-Ph-CH$_3$), 2.24 (H-7a), 2.09 (H-7b), 1.91 (H-4), 1.83 (H-4'a), 1.68 (H-14a), 1.52 (H-2"b), 1.41 (H-14b), 1.49 (6-CH$_3$), 0.89 (H-15).

Compound (3f)

$^1$H NMR (300 MHz, CDCl$_3$) δ7.43 (p-Ph), 7.14 (SO$_2$NH), 4.91 (H-13), 4.78 (H-1"), 4.60 (H-1'), 4.36 (H-3), 4.00 (H-5"), 3.82 (H-5), 3.73 (H-10), 3.68 (H-5'), 3.64 (H-11), 3.41 (H-2'), 3.28 (3"-OCH-$_3$), 3.08 (H-8), 3.00 (H-4"), 2.79 (H-2), 2.39 (p-Ph-CH$_3$), 2.24 (H-2"), 1.73 (H-14a), 1.52 (6-CH$_3$), 0.85 (H-15).

EXAMPLE 5

6-Deoxy-6,9-epoxy-8(R)-methyl-10-amino-9,10-secoerythromycin A (2a)

Method A

An erythromycin A 6,9-imino ether solution (1) (10.0 g, 0.014 mole) in glacial acetic acid (60 ml) was left to stand for 3 days at room temperature. The solvent was evaporated at a reduced pressure and then water (100 ml) was added to the oily residue and the reaction mixture was extracted with CHCl$_3$ at pH 5.5, 6.5 and 8.3. After drying over K$_2$CO$_3$ the combined organic extracts at pH 8.3 were evaporated to dryness and the obtained product was dried in a high vacuum (6 hours, 40° C.), whereupon 8.2 g (80.0%) of TLC homogeneous product (2a) were obtained.

IR (CHCl$_3$) cm$^{-1}$: 1740 (C-1, lactone) and 1710 (C-9, lactone). $^1$H NMR (300 MHz, CDCl$_3$) δ: 4.77 (H-1"), 5.00 (H-13), 4.39 (H-1'), 4.18 (H-3), 3.74 (H-5), 3.35 (H-11), 3.29 (H-3"-OCH$_3$), 3.16 (H-10), 2.76 (H-8), 2.72 (H-2), 2.29/3'N(CH$_3$)$_2$/, 2.22 (H-7a), 2.10 (H-7b), 2.00 (H-4), 1.85 (H-14a), 1.55 (H-14b), 0.88 (H-15). $^{13}$C NMR, (75 MHz, CDCl$_3$) δ: 179.6 (C-1), 176.1 (C-9), 103.9 (C-1'), 95.7 (C-1"), 86.1 (C-6), 81.2 (C-5), 78.8 (C-13), 77.9 (C-3), 75.7 (C-11), 74.5 (C-12), 49.5 (3"-OCH$_3$), 47.9 (C-10), 43.2 (C-2), 40.4/3'N(CH$_3$)$_2$/, 39.7 (C-4), 38.0 (C-7), 34.1 (C-8), 22.2 (C-14, 11.6 (C-15). EI-MS (M$^+$) 748.

Method B

A solution of (3a) (2.0 g, 0.0026 mole) in methanol (30 ml) was acidified with 1N HCl to pH 3.0 and left to stand for 10 days at room temperature. The pH of reaction mixture was adjusted to 7.0 with 10% NaOH, methanol was evaporated at a reduced pressure, to the aqueous residue CHCl$_3$ was added and then it was extracted at pH 5.5, 6.5 and 8.3. After drying ever K$_2$CO$_3$ the combined organic extracted at pH 8.3 were evaporated to dryness, yielding the product (2a) with the identical physical-chemical constants as described at Method A.

EXAMPLE 6

2', 4",11-O,10-N-tetraacetyl-6-deoxy-6,9-epoxy-8 (R) -methyl-10-amino-9,10-secoerythromycin A (2b)

To a solution of (2a)(3.4 g, 0.0045 mole) in pyridine (45 ml), acetic acid anhydride (12 ml) was aded and it was left to stand for 7 days at room temperature. After completed acetylation reaction (TLC), the reaction mixture was poured onto ice (200 ml) and extracted with CHCl$_3$ at pH 9.0. The combined organic extracts were washed with saturated NaHCO$_3$ solution and water, dried over K$_2$CO$_3$ and evaporated at a reduced pressure. The obtained crude residue was dried in a high vacuum (6 hours, 40° C.) yielding 4.10 g (98.0 %) of chromatographically homogeneous product (2b).

IR (CHCl$_3$) cm$^{-1}$: 1740 (C-1, lactone), 1720 (C-6, lactone), 1720 and 1240 (C=O, ester), 1655 (C=O, amide). $^1$H NMR (300 MHz, CDCl$_3$) δ: 6.35 (CONH), 4.99 (H-13), 4.79 (H-1"), 4.79 (H-2'), 4.68 (H-11), 4.62 (H-1'), 4.44 (H-10), 4.14 (H-3), 3.76 (H-5), 3.32 (H-3"-OCH$_3$), 2.74 (H-8), 2.65 (H-2), 2.28 /3'N(CH$_3$)$_2$/, 2.10, 2.06, 2.03 and 1.92 (COCH$_3$), 2.08 (H-7a), 1.96 (H-7b), 1.90 (H-4), 1.81 (H-14a), 1.60 (H-14b), 0.86 (H-15). $^-$C NMR (75 MHz, CDCl$_3$) δ:179.3 (C-1), 174.7 (C-9), 171.9 170.5, 169.9 and 169.2 (COCH$_3$). EI-MS (M$^+$) 916.

EXAMPLE 7

4",11-O,10 -N-triacetyl-6-deoxy-6,9-epoxy-8(R) -methyl-10-amino-9,10-secoerythromycin A (2c)

A solution of (2b) (1.5 g, 0.0016 mole) in methanol (40 ml) was left to stand for 3 days at room temperature. The reaction mixture was evaporated at reduced pressure and the obtained oily residue was dissolved in CH$_2$Cl$_2$ (50 ml), then 100 ml of water were added (pH 6.6) and the pH of the reaction mixture was adjusted to 9.0 with 10% w/v NaOH. The layers were separated and the aqueous part was extracted two more times with $CH_2Cl_2$. After the drying of the combined organic extracts over $K_2CO_3$ and evaporation of the solvent at a reduced pressure, there were obtained 1.35 g of a crude product, which was purified by chromatography on silica get column by the use of 6:1:0.1 $CHCl_3:CH_3OH$:conc. $NH_4OH$ system yielding TLC homogeneous triacetate (2c) with the following physical-chemical constants:

$^1$H NMR (300 MHz, $CDCl_3$) δ: 6.39 (CONH), 4.99 (H-13), 4.79 (H-1"), 4.68 (H-4"), 4.66 (H-11), 4.48 (H-1'), 4.46 (H-10), 4.21 (H-3), 3.76 (H-5), 3.30 (3"-$OCH_3$), 3.23 (H-2'), 2.75 (H-8), 2.70 (H-2), 2.29/3'N($CH_3$)$_2$/, 2.26 (H-7a), 2.16, 2.12 and 1.96 ($COCH_3$), 2.02 (H-7b), 1.94 (H-4), 1.83 (H-14a), 1.56 (H-14b), 0.86 (H-15). $^{13}$C NMR (75 MHz, $CDCl_3$) δ: 179.2 (C-1), 174.6 (C-9), 171.7, 170.3 and 169.0 ($COCH_3$), 102.9 (C-1'), 94.9 (C-1"), 85.6 (C-6), 80.5 (C-5), 78.3 (C-3), 78.2 (C-11), 76.7 (C-13), 74.7 (C-12), 49.2 (3"-$OCH_3$), 45.1 (C-10), 42.4 (C-2), 40.0/3'N($CH_3$)$_2$/, 39.3 (C-4), 37.3 (C-7), 33.9 (C-8), 21.9 (C-14), 21.1, 20.9 and 20.6 ($COCH_3$), 10.7 (C-15).

EXAMPLE 8

10-N-(4-bromobenzoyl)-6-deoxy-6,9-epoxy-8(R)-methyl-10-amino-9,10-secoerythromycin A (2d)

To a solution of 10 g (0.013 mole) of (2a) in diethylether (60 ml & $NaHCO_3$ (8.0 g, 0.095 mole), 4-bromobenzoylchloride solution (4.0 g, 0.018 mole) in diethylether (20 ml) was added dropwise within 1 hour under stirring at a temperature from 0° to 5° C. The reaction mixture was stirred for further 2 hours at the same temperature, the solvent was evaporated at a reduced pressure, then $CHCl_3$ (70 ml) and water (50 ml) were added m the obtained solid residue and then it was extracted at pH 8.5. The reaction mixture was evaporated at a reduced pressure and the obtained solid residue (5.0 g) was purified by chromatography on silica gel column by the use of 90:9:1.5 $CH_2Cl_2:CH_3OH$:conc. $NH_4OH$ system yielding TLC homogeneous 4-bromobenzoate (2d) with the following physical-chemical constants:

IR ($CHCl_3$) cm$^{-1}$: 1740 (C-1, lactone), 1710 (C-9, lactone), 1640 and 1500 (C-10, amide), 1580 (Ph). , 4.91 (H-13), 4.70 (H-1"), $^1$H NMR 9300 MHz, $CDCl_3$) δ: 7.60 (Ph), 7.05 CONH, 4.35 (H-1'), 4.37 (H-10), 4.21 (H-3), 3.70 (H-5), 3.67 (H-11), 3.27 (3"-$OCH_3$), 3.15 (H-2'), 2.91 (H-4"), 2.73 (H-8), 2.71 (H-2), 2.26/3'N($CH_3$)$_2$/, 2.21, (H-7a), 2.10 (H-7b), 1.94 (H-4), 1.86 (H-14a), 1.57 (H-14b), 0.89 (H-15). $^{13}$C NMR (75 MHz, $CDCl_3$) δ: 179.6 (C-1), 176.7 (C-9), 165.4 (CONH), 133.8, 131.6, 128.9 and 125.8 (Ph), 104.0 (C-1'), 95.0 C-1"), 86.4 (C-6), 81.7 (C-5), 79.9 (C-3), 75.6 (C-13), 73.4 (C-11), 74.6 (C-12), 49.4 (3"-$OCH_3$), 47.3 (C-10), 43.2 (C-2), 40.0 /3'N($CH_3$)$_2$/, 40.0 (C-4), 37.8 (C-7), 34.2 (C-8), 22.5 (C-14), 11.2 (C-15). EI-MS (M$^+$) 931.

EXAMPLE 9

1N-(2,3,4-trihydroxy-1,3-dimethyl-hexyl)-amido-10,11,12,13,14,15-hexanor-9-deoxo-6-deoxy-6,9-epoxy-8(R)-methyl-9,10-secoerythromycin A 9(E) Oxime (4a)

The substance (3a) (31 g, 0.041 mole) from Example 1 was dissolved in $CH_2Cl_2CH_3OH$ (1:1, 80 ml), thereto conc. $NH_4OH$ (350 ml) was added and the reaction mixture was stirred for 6 hours at room temperature. The solution was left to stand overnight and then it was evaporated at a reduced pressure and the obtained solid residue was suspended in $CH_2Cl_2$, filtered and subsequently the filtrate was evaporated to dryness yielding 29.5 g (95%) of TLC ($CHCl_3:CH_3OH$:conc. $NH_4OH$, 6:1:0.1) homogeneous product (4a).

IR ($CHCl_3$) cm$^{-1}$: 3420, 2980, 1690, 1650, 1530, 1455, 1380, 1260, 1175, 1050. $^1$H NMR (300 MHz, $CDCl_3$) δ: 7.53 (CONH), 4.93 (H-1"), 4.45 (H-1'), 4.20 (H-3), 4.11 (H-10), 3.79 (H-11), 3.66 (H-5), 3.39 (3'-$OCH_3$), 3.22 (H-13), 3.04 (H-8), 2.53 (H-2), 2.29/3'N($CH_3$)$_2$/, 2.10 (H-7a), 1.97 (H-4), 1.79 (H-7b), 1.59 (H-14a), 1.33 (H-14b), 1.04 (H-15). $^{13}$C NMR (75 MHz, $CDCl_3$) δ:174.4 (C-1), 162.0 (C-9), 105.6 (C-1'), 96.2 (C-1"), 90.3 (C-6), 86.3 (C-5), 83.0 (C-13), 79.8 (C-3), 75.1 (C-11), 74.9 (C-12) 49.3 (3"-$OCH_3$), 48.6 (C-10), 42.8 (C-2), 41.0 (C-7), 39.8 /3'N ($CH_3$)$_2$/, 38.6 (C-4), 32.9 (C-8), 24.8 (C-14), 11.5 (C-15). FAB (MH$^+$) 764.4.

EXAMPLE 10

1N-(2,3,4-trihydroxy-1,3-dimethyl-hexyl)-amido-10,11,12,13,14,15-hexanor-9-deoxo-6-deoxy-6,9-epoxy-8(R)-methyl-9,10-secoerythromycin A 9(E) Oxime (4a)

1-N-(2,3,4,-trihydroxy-1,3-dimethyl-hexyl)-amido-10,11,12,13,14,15-hexanor-9-deoxo-6-deoxy-6,9-epoxy-8(S)-methyl-9,10-secoerythromycin A 9(E) Oxime (4b)

Erythromycin A 6,9-imino ether (1) (30 g, 0.041 mole) was dissolved in $CH_3OH$ (600 ml), $Na_2CO_3$ (5.6 g, 0.053 mole) was added thereto and then the reaction mixture was stirred under reflux up to the disappearance of the starting imino ether (8 hours.) The reaction suspension was evaporated at a reduced pressure, thereto $CH_2Cl_2$ (130 ml) and $H_2O$ (130 ml) were added (pH 11.1) and then it was extracted at pH 8. The combined organic extracts were dried over $K_2CO_3$ and evaporated whereby 28 g of solid residue were obtained. The precipitate was dissolved in $CH_3OH$ (600 ml), thereto $NH_2OH.HCl$ (14 g) and $Na_2CO_3$ (5.1 g) were added and then it was stirred under reflux for 3 hours. The reaction mixture was evaporated to dryness, $CH_2Cl_2$ (150 ml) and $H_2O$ (300 ml) were added thereto (pH 6.6) and it was extracted by gradient extraction at pH 8 and 10. The combined orgainic extracts at pH 10 were dried over $K_2CO_3$ and evaporated, whereby 15.6 g of precipitate were obtained. The precipitate was dissolved in a mixture of $CH_3OH$—$CH_2Cl_2$ (1:1, 40 ml) and conc. $NH_4OH$ (170 ml) and stirred for 12 hours at room temperature. The reaction mixture was evaporated to dryness and the obtained mixture of products was separated by chromatography on silica gel column. From 2.2 g of a crude product there were obtained by the use of 6:1:0.1 $CHCl_3:CH_3OH$:conc. $NH_4OH$ system, 1.08 g of a chromatographically homogeneous product (4a) (Rf 0.38) with physical-chemical constants as described in Example 9 and 0.80 g of a substance (4b) (Rf 0.26) with the following physical-chemical constants:

Compound (4b)

IR ($CHCl_3$) cm$^{-1}$: 3340, 1975, 1685, 1650, 1530, 1450, 1380, 1280, 1240, 1160, 1040. $^1$H NMR (300 MHz, $CDCl_3$) δ: 7.30 (CONH), 4.88 (H-1"), 4.35 (H-1'), 4.23 (H-3), 4.15 (H-10), 3.82 (H-11), 3.60 (H-5), 3.29 (3"-$OCH_3$), 3.26 (H-13), 3.14. (H-8), 2.78 (H-7a), 2.52 (H-2), 2.29/3'N($CH_3$)

_/, 2.06 (H-4), 1.61 (H-14a), 1.51 (H-7b), 1.37 (H-14b), 1.04 (H-15). $^{13}$C NMR (75 MHz, CDCl$_3$) δ:173.9 (C-1), 162.7 (C-9), 104.6 (C-1'), 95.4 (C-1"), 90.7 (C-6), 86.3 (C-5), 81.6 (C-13), 78.5 (C-3), 74.5 (C-11), 74.4 (C-12) 48.8 (3"-OCH$_3$), 47.4 (C-10), 42.7 (C-2), 42.0 (C-7), 39.4 /3'N(CH$_3$)$_2$/, 38.7 (C-4), 33.8 (C-8), 24.1 (C-14), 11.0 (C-15). FAB (MH$^+$) 764.5.

EXAMPLE 11

2',4"-O-diacetyl-1-N-(2,4-O-dimethyl-3-hydroxy-1, 3-dimethyl-hexyl)-amido-10,11,12,13,14,15-hexanor-9-deoxo-6-deoxy-6,9-epoxy-8(R)-(R)-methyl-9,10-secoerythromycin A 9(E) Acetoxime (4c)

To a solution of the substance (4a) (1.0 g, 0.0013 mole) from example 9 in pyridine (40 ml), acetic acid anhydride (4 ml) was added and then it was left to stand for 10 days at room temperature. The reaction solution was poured into a mixture 200 of water and ice (pH 4.8), alkalinized with 20% NaOH and then extracted with CHCl$_3$ at pH 9.0. The combined organic extracts were dried over K$_2$CO$_3$ and evaporated at a reduced pressure yielding 1.25 g (98%) of pentaacetate (4c) with the following physical-chemical constants:

$^1$H NMR (300 MHz, CDCl$_3$) δ: 6.61 (CONH), 4.94 (H-13), 4.82 (H-1"), 4.80 (H-2'), 4.69 (H-4'), 4.58 (H-1'), 4.58 (H-10), 4.55 (H-11), 4.04 (H-3), 3.79 (H-5), 3.32 (3"-OCH$_3$), 3.13 (H-8), 2.59 (H-2), 2.27/3'N(CH$_3$)$_2$/, 2.15, 2.12, 2.12, 2.06 and 2.01 (COCH$_3$), 2.07 (H-7a), 2.03 (H-4), 2.03 (H-7b), 1.82 (H-14a), 1.55 (H-14b), 0.90 (H-15). $^{13}$C NMR (75 MHz, CDCl$_3$) δ: 173.4 (C-1), 171.8, 170.6, 170.2, 169.8, and 168.8 (COCH$_3$), 167.2 (C-9), 100.6 (C-1'), 95.5 (C-1"), 91.7 (C-6), 79.8 (C-3), 79.6 (C-5), 78.6 (C-11), 75.7 (C-13), 74.7 (C-12) 49.3 (3"-OCH$_3$), 45.1 (C-10), 42.6 (C-2), 40.2/3'N(CH$_3$)$_2$/, 38.8 (C-7), 36.7 (C-4), 33.5 (C-8), 21.6 (C-14), 20.9, 20.5, 20.5, 20.4 and 19.4 (COCH$_3$), 10.5 (C-15).

EXAMPLE 12

4"-O-acetyl-1-N-(2,4-O-diacetyl-3-hydroxy-1,3-dimethyl-hexyl)-amido-10,11,12,13,14,15-hexanor-9-deoxo-6-deoxy-6,9-epoxy-8(R)-methyl-9,10-secoerythromycin A 9(E) Acetoxime (4d)

4"-O-acetyl-1-N-(2,4,-O-diacetyl-3-hydroxy-1,3-dimethyl-hexyl)-amido-10,11,12,13,14,15-hexanor-9-deoxo-6-deoxy-6,9-epoxy-8(R)-methyl-9,10-secoerythromycin A 9(E)Oxime (4e)

A solution of 0.5 g (0.0005 mole) of the substance (4c) from Example 11 in methanol (20 ml) was stirred for 3 days at room temperature. The solvent was separated by evaporation at a reduced presure and the obtained mixture was purified by chromatography on silica gel column by the use of 6:1:0.1 CHCl$_3$:CH$_3$OH:conc. NH$_4$OH solvent system. After the evaporation of chromatographically homogeneous fractions with Rf 0.47 and Rf 0.34, there were obtained 0.213 g of tetraacetate (4d) and 0.151 g of triacetate (4e) with the following physical-chemical constants:

Compound (4d)

$^1$H NMR (300 MHz, CDCl$_3$) δ: 7.38 (CONH), 4.94 (H-13), 4.83 (H-1"), 4.66 (H-4"), 4.62 (H-11), 4.55 (H-10), 4.44 (H-1'), 4.10 (H-3), 3.80 (H-5), 3.32 (3"-OCH$_3$), 3.35 (H-2'), 3.18 (H-8), 2.76 H-2), 2.30/3'N(CH$_3$)$_2$/, 2.07 (H-7a), 2.13, 2.10, 2.09 and 2.03 (COCH$_3$), 1.90 (H-7b), 1.96 (H-4), 1.84 (H-14a), 1.53 (H-14b), 0.90 (H-15). $^{13}$C NMR (75 MHz, CDCl$_3$) δ: 174.4 (C-1), 171.1, 170.7, 170.4 and 168.4 (COCH$_3$), 167.2 (C-9), 105.2 (C-1'), 96.9 (C-1"), 92.9 (C-6), 84.5 (C-5), 81.3 (C-3), 78.5 (C-11), 75.9 (C-13) 75.0 (C-12), 49.4 (3"-OCH$_3$), 44.6 (C-10), 41.1 (C-2), 40.1 /3'N(CH$_3$)$_2$/, 40.8 (C-7), 38.0 (C-4), 33.8 (C-8), 21.7 (C-14), 20.7, 20.5, 20.4 and 19.2 (COCH$_3$), 10.5 (C-15).

Compound (4e)

$^1$H NMR (300 MHz, CDCl$_3$) δ: 7.24 (CONH), 4.88 (H-13), 4.81 (H-1"), 4.68 (H-4"), 4.62 (H-11), 4.50 (H-10), 4.45 (H-1'), 4.07 (H-3), 3.75 (H-5), 3.34 (3"-OCH$_3$), 3.26 (H-2'), 2.98 (H-8), 2.76 (H-2), 2.30/3'N(CH$_3$)$_2$/, 2.09 (H-7a), 2.14, 2.09 and 2.03 (COCH$_3$), 1.92 (H-7b), 1.89 (H-4), 1.83 (H-14a), 1.51 (H-14b), 0.89 (H-15). $^{13}$C NMR (75 MHz, CDCl$_3$) δ: 174.6 (C-1), 171.1, 170.8, 170.8 (COCH$_3$), 162.5 (C-9), 104.2 (C-1'), 96.4 (C-1"), 90.4 (C-6), 83.9 (C-5), 79.6 (C-3), 78.7 (C-11), 76.1 (C-13) 75.1 (C-12), 49.5 (3"-OCH$_3$), 44.7 (C-10), 43.7 (C-2), 40.1 /3'N(CH$_3$)$_2$/, 40.4 (C-7), 39.3 (C-4), 32.5 (C-8), 21.8 (C-14), 20.7, 20.7 and 20.6 (COCH$_3$), 10.7 (C-15).

EXAMPLE 13

1-N-(2,3,4,-trihydroxy-1,3-dimethyl-hexyl)-amido-10,11,12,13,14,15-hexanor-9-deoxo-6-deoxy-6,9-epoxy-8(R)-methyl-9,10-secoerythromycin A 9(E) Tosyloxime (4f)

The substance (4a) (0.5 g, 0.0007 mole) from Example 9 was suspended in acetone (10 ml) and cooled to 0°–5° C. Solutions of tosylchloride (0.486 g, 0.0026 mole) in acetone (10 ml) and NaHCO$_3$ (0.425 g, 0.0051 mole) in water (25 ml) were simultaneously added dropwise to the reaction mixture under stirring within 30 minutes. The reaction solution was stirred for further 12 hours at room temperature, thereafter acetone was evaporated at a reduced pressure, to the aqueous residue CHCl$_3$ (30 ml) was added and then it was extracted by gradient extraction at pH 5.0 and 8.0. By evaporation of the combined organic extracts at pH 5.0, 0.320 g of crude product (4f) were obtained. By chromatography on silica gel column by the use of 6:1:0.1 CHCl$_3$:CH$_3$OH:conc. NH$_4$OH, 0.260 g of TLC homogeneous product (4f) were obtained. $^1$H NMR (300 MHz, CDCl$_3$) δ: 7.80 (CONH), 7.62 (Ph), 3.21 (H-13), 4.96 (H-1"), 4.41 (H-1'), 4.17 (H-3), 4.11 (H-10), 3.79 (H-11), 3.58 (H-5), 3.39 (H-2'), 3.25 (3"OCH$_3$), 3.10 (H-8), 2.94 (H-4"), 2.55 (H-2), 2.29/3'N(CH$_3$)$_2$/, 2.08 (H-7a), 1.86 (H-4), 1.64 (H-7b), 1.56 (H-14a), 1.43 (H-14b), 1.05 (H-15).

EXAMPLE 14

1-N-(2,3,4-trihydroxy-1,3-dimethyl-hexyl)-amido-10,11,12,13,14,15-hexanor-9-deoxo-9-dihydro-9a-amino-8(R)-methyl-9a-homoerythromycin A (5a)

The crude product (4a) (6.0 g, 0.008 mole) from Example 9 was dissolved in glacial acetic acid (60 ml), PtO$_2$ (2.0 g, 83.0% Pt) were added and then it was hydrogenated at a H$_2$ pressure of 7×10$^6$ Pa under stirring within 10 hours. The reaction suspension was filtered, the filtrate was evaporated at a reduced pressure, H$_2$O (100 ml) and CHCl$_3$ (60 ml) were added thereto and subsequently it was extracted by gradient extraction at pH 5.5, 9.0 and 10.5. The combined chloroform extracts at pH 10.5 were evaporated at a reduced pressure fielding 4.3 g (73%) of TLC homogeneous product (5a) with the following physical-chemical constants:

IR (CHCl$_3$) cm$^{-1}$: 3400, 2975, 1650, 1535, 1450, 1375, 1165, 1040. $^1$H NMR (300 MHz, CDCl$_3$) δ: 7.52 (CONH), 4.94 (H-1"), 4.37 (H-1'), 4.26 (H-3), 4.17 (H-10), 3.76 (H-11), 3.41 (H-5), 3.28 (3"-OCH3), 3.17 (H-13), 2.62 (H-9a), 2.52 (H-2), 2.27/3'N(CH$_3$)$_2$/, 2.20 (H-7a), 2.01 (H-4), 1.85 (H-8), 1.55 (H-14a), 1.34 (H-7b), 1.34 (H-14b), 1.05 (H-15). $^{13}$C NMR (75 MHz, CDCl$_3$) δ:174.1 (C-1), 106.7 (C-1'), 96.0 (C-1"), 92.3 (C-5), 83.8 (C-13), 79.7 (C-3), 75.1 (C-12), 74.8 (C-11) 74.6 (C-6), 49.3 (3"-OCH$_3$), 49.2 (C-10), 49.1 (C-9), 42.8 (C-7), 41.6 (C-2), 39.6/3'N (CH$_3$)$_2$/, 37.5 (C-4), 31.0 (C-8), 25.0 (C-14), 11.5 (C-15). FAB (NH$^+$) 752.3.

EXAMPLE 15

1-N-(2,3,4-trihydroxy-1,3-dimethyl-hexyl)-amido-10,11,12,13,14,15-hexanor-9-deoxo-9-dihydro-9a-amino-8(S)-methyl-9a-homoerythromycin A (5b)

The substance (4b) (0.71 g, 0.009 mole) was dissolved in glacial acetic acid (30 ml), PtO$_2$ (0.350g, 83% Pt) was added and then it was hydrogenated under stirring for 10 hours at a H$_2$ pressure 7×10$^6$ Pa. The reaction mixture was filtered, the filtrate was evaporated to a thick oily residue and the product was isolated by gradient extraction at pH 5.5, 9.0 and 10.5 as described in Example 14, whereupon after the evaporation of the combined organic extracts at pH 10.5, 0.260 g (38.0%) of TLC homogeneous title product (5b) were obtained.

$^1$H NNR (300 MHz, CDCl$_3$) δ: 7.63 (CONH), 4.93 (H-1"), 4.40 (H-1'), 4.23 (H-3), 4.19 (H-10), 3.75 (H-11), 3.53 (H-5), 3.29 (3"-OCH$_3$) 3.18 (H-13), 2.72 (H-9a), 2.57 (H-9b), 2.52 (H-2), 2.27/3'N(CH$_3$)$_2$/, 1.93 (H-4), 1.78 (H-8), 1.57 (H-14a), 1.47 (H-7a), 1.36 (H-14b), 1.23 (H-7b), 1.04 (H-15). $^{13}$C NMR (75 MHz, CDCl$_3$) δ: 174.3 (C-1), 107.2 (C-1'), 97.0 (C-1"), 92.3 (C-5), 83.8 (C-13), 80.7 (C-3), 75.7 (C-12), 75.2 (C-11), 75.2 (C-6), 49.6 (3"-OCH$_3$), 49.2 (C-9), 49.2 (C-10), 43.7 (C-7), 42.1 (C-2), 39.8/3'N(CH$_3$)$_2$/, 37.8 (C-4), 31.3 (C-8), 25.0 (C-14), 11.7 (C-15).

EXAMPLE 16

1-N-(2,3,4-trihydroxy-1,3-dimethyl-hexyl)-amido-10,11,12,13,14,15-hexanor-9-deoxo-9-dihydro-9a-dimethylamino-8(R)-methyl-9a-homoerythromycin A (6a)

To a solution of compound (5a) (1 g, 0.0013 mole) from Example 14 in CHCl$_3$ (80 ml), 0.2 ml (0.005 mole) of formic acid (98–100%) and 0.232 ml (0.003 mole) of formaldehyde (36%) were added. The pH of the reaction mixture was adjusted to 5.0 (with 2% w/v NaOH) and then it was stirred under reflux for 9 hours. Subsequently the addition of H$_2$O (100 ml), the product was isolated by gradient extraction with CHCl$_3$ at pH 5.0 and 9.5 and the combined organic extracts at pH 9.5 were evaporated at a reduced pressure. By chromatography of the obtained product on silica gel column by the use of 6:1:0.1 CHCl$_3$:CH$_3$OH:conc. NH$_4$OH system, 0.63 g of TLC homogeneous product (6a) were obtained.

IR (CHCl$_3$) cm$^{-1}$: 3400, 2970, 1650, 1530, 1450, 1375, 1165, 1040. $^1$H NMR (300 MHz, CDCl$_3$) δ: 7.26 (CONH), 4.91 (H-1"), 4.37 (H-1'), 4.27 (H-3), 4.18 (H-10), 3.77 (H-11), 3.41 (H-5), 3.29 (3"-OCH$_3$), 3.18 (H-13), 2.57 (H-2), 2.52 (H-9a), 2.30/3'N(CH$_3$)$_2$/, 9a-N(CH$_3$)$_2$/, 2.20 (H-9b), 2.16 (H-4), 2.01 (H-8), 1.56 (H-14a), 1.50 (H-7a), 1.37 (H-14b), 1.15 (H-7b), 1.04 (H-15). $^{13}$C NMR (75 MHz, CDCl$_3$) δ: 174.7 (C-1), 106.1 (C-1'), 95.4 (C-1"), 90.5 (C-5), 83.3 (C-13), 79.8 (C-3), 74.8 (C-12), 74.6 (C-11), 73.7 (C-6), 68.2 (C-9), 49.2 (3"-OCH$_3$), 48.6 (C-10), 45.3/9a-N (CH$_3$)$_2$/, 44.2 (C-7), 41.7 (C-2), 39.6/3'N(CH$_3$)$_2$/, 37.3 (C-4), 26.4 (C-8), 24.9 (C-14); 11.5 (C-15). FAB (MH$^+$) 780.6.

EXAMPLE 17

1-N-(2,3,4-trihydroxy-1,3-dimethyl-hexyl)-amido-10,11,12,13,14,15-hexanor-9-deoxo-9-dihydro-9a-dimethylamino-8(S)-methyl-9a-homoerythromycin A (6b)

To a solution of the compound (5b) (0.3 g, 0.0004 mole) from Example 15 in CHCl$_3$ (50 ml), 0.12 ml (0.0032 mole) of formic acid (98–100%) and 0.13 ml (0.0016 mole) of formaldehyde (36%) were added. The pH of the reaction mixture was adjusted to 5.0 (with 2% w/v NaOH) and then it was stirred under reflux for 4 hours. The isolation of the product was performed as described in Example 16, yielding after chromatography on silica gel column by the use of 6:1:0.1 CHCl$_3$:CH$_3$OH:conc. NH$_4$OH system 0.150 g of TLC homogeneous product (6b).

$^1$H NMR (300 MHz, CDCl$_3$) δ: 7.58 (CONH), 4.95 (H-1"), 4.41 (H-1'), 4.25 (H-3), 4.18 (H-10), 3.76 (H-11), 3.43 (H-5), 3.28 (3"-OCH$_3$), 3.17 (H-13), 2.51 (H-2), 2.27/3'N(CH$_3$)$_2$/, 2.23/9a-N(CH$_3$)$_2$/, 2.06 (H-9b), 2.19 (H-4), 1.97 (H-8), 1.57 (H-14a), 1.47 (H-7a), 1.37 (H-14b), 1.16 (H-7b), 1.05 (H-15). $^{13}$C NMR (75 MHz, CDCl$_3$) δ: 173.5 (C-1), 106.0 (C-1'), 95.3 (C-1"), 91.9 (C-5), 83.2 (C-13), 79.0 (C-3), 74.4 (C-12), 74.1 (C-11), 74.2 (C-6), 67.5 (C-9), 48.6 (3"-OCH$_3$), 48.4 (C-10), 44.9 /9-N(CH$_3$)$_2$/, 43.1 (C-7), 40.8 (C-2), 38.9 /3'N(CH$_3$)$_2$/, 36.7 (C-4), 25.8 (C-8), 23.9 (C-14), 10.4 (C-15).

EXAMPLE 18

9-Deoxo-6-deoxy-6,9-epoxy-8(R)-methyl-10,11,12,13,14,15-hexanor-erythromycin A 9(E) Oxime (7a)

9-Deoxo-6-deoxy-6,9-epoxy-8(S)-methyl-10,11,12,13,14,15-hexanor-erythromycin A 9(E) Oxime (7b)

The combined chloroform extracts at pH 8 from Example 10 were dried over K$_2$CO$_3$ and evaporated at a reduced pressure yielding 8.0 g of mixture of (7a) and (7b). By chromatography on silica gel column by the use of 6:1:0.1 CHCl$_3$:CH$_3$OH:conc. NH$_4$OH system, from 2.0 g of a crude product there were obtained 0.530 g of substance (7a) with Rf 0.44 and 0.880 g of substance (7b) with 0.39 which were identified by spectrascopic methods as C-8 stereoisomers.

Compound (7a)

IR (CHCl$_3$) cm$^{-1}$: 3360, 2980, 2940, 1730, 1690, 1650, 1455, 1380, 1245, 1165, 1040. $^1$H NMR (300 MHz, CDCl$_3$) δ: 4.72 (H-1"), 4.44 (H-1'), 4.11 (H-3), 3.84 (H-5), 3.67 (1-OCH$_3$), 3.29 (3"-OCH$_3$), 3.26 (H-2'), 3.03 (H-8), 3.01 (H-4"), 2.84 (H-2), 2.09 ((H-7a), 2.33/3'N(CH$_3$)$_2$/, 1.97 (H-4), 2.01 (H-7b). $^{13}$C NMR (75 MHz CDCl$_3$) δ: 176.1 (C-1), 161.8 (C-9), 103.8 (C-1'), 95.8 (C-1"), 89.7 (C-6), 81.0 (C-5), 79.8 (C-3), 51.8 (1-OCH$_3$), 49.4 (3"-OCH$_3$), 39.9 (C-7), 41.7 (C-2), 40.4/3'N(CH$_3$)$_2$/, 37.8 (C-4), 33.0 (C-8). FAB (MH$^+$) 619.4.

Compound (7b)

IR (CHCl$_3$) cm$^{-1}$: 3360, 2980, 2940, 1730, 1690, 1650, 1455, 1380, 1245, 1165, 1040. $^1$H NMR (300 MHz, CDCl$_3$) δ: 4.61 (H-1"), 4.43 (H-1'), 4.09 (H-3), 3.71 (H-5), 3.68

(1-OCH₃), 3.28 (3"-OCH₃), 3.17 (H-8), 2.89 (H-7a), 2.74 (H-2), 2.33/3'N(CH₃)₂/, 2.16 (H-4), 1.47 (H-7b). ¹³C NMR (75 MHz, CDCl₃) δ:176.0 (C-1), 1.62.9 (C-9), 102.7 (C-1'), 95.1 (C-1") 90.4 (C-6), 80.1 (C-5), 79.0 (C-3), 51.6 (1-OCH₃), 49.2 (3"-OCH₃), 42.5 (C-7), 41.0 (C-2), 40.3/ 3'N(CH₃)₂/, 38.1 (C-4), 34.5 (C-8).

EXAMPLE 19

9-Deoxo-9-dihydro-9a-amino-8(R)-methyl-10,11,12, 13,14,15-hexanor-9a-homoerythromycin A (8a)

The substance (7a) (0.90 g, 0.0015 mole) was dissolved in glacial acetic acid (30 ml), PtO₂ (0.30 g, 83% Pt) was added thereto and then it was hydrogenated at H₂ pressure of 6×10⁶ Pa under stirring for 15 hours. The reaction mixture was filtered, the filtrate was evaporated to a thick oily residue and a product was isolated by gradient extraction at pH 5.5, 9.0 and 10.5 as described in Example 14, whereupon after the evaporation of the combined organic extracts at pH 10.5, 0.530 g (60%) of TLC homogeneous title product (8a) were obtained.

¹H NMR (300 MHz, CDCl₃) δ: 4.64 (H-1"), 4.40 (H-1'), 4.14 (H-3), 3.67 (1-OCH₃), 3.54 (H-5), 3.29 (H-3"OCH₃), 2.85 (H-2), 2.74 (H-9a), 2.50 (H-9b), 2.30/3'N(CH₃)₂/, 2.10 (H-4), 1.84 (H-8), 1.44 (H-7a), 1.22 (H-7b). ¹³C NMR (75 MHz, CDCl₃) δ:176.4 (C-1), 104.4 (C-1'), 96.0 (C-1"), 85.9 (C-5), 80.3 (C-3), 73.8 (C-6), 51.5 (1-OCH₃), 49.2 (3"-OCH₃), 49.1 (C-9), 42.9 (C-7), 41.2 (C-2) 40.2/3'N(CH₃)₂, 37.3 (C-4), 31.1 (C-8).

EXAMPLE 20

9-Deoxo-9-dihydro-9a-amino-8(S)-methyl-10,11,12, 13,14,15-hexanor-9a-homoerythromycin A (8b)

The substance (7b) (0.70 g, 0.0011 mole) was dissolved in glacial acetic acid (25 ml), PtO₂ (0.23 g, 83% Pt) was added thereto and then it was hydrogenated at H₂ pressure of 6×10⁶ Pa under stirring for 15 hours. The reaction mixture was filtered, the filtrate was evaporated to a thick oily residue and a product was isolated by gradient extraction at pH 5.5, 9.0 and 10.5 as described in Example 14, whereupon after the evaporation of the combined organic extracts at pH 10.5, 0.350 g (52.4%) of TLC homogeneous title product (8b) were obtained.

IR (CHCl₃) cm⁻¹: 3400, 2975, 2940, 1735, 1580, 1455, 1375, 1260, 1170, 1050, 1000. ¹H NMR (300 MHz, CDCl₃) δ:4.64 (H-1"), 4.37 (H-1'), 4.15 (H-3), 4.04 (H-5"), 3.67 (1-OCH₃, 3.60 (H-5'), 3.51 (H-5), 3.37 (H-2'), 3.28 (H-3"OCH₃), 2.98 (H-4"), 2.75 (H-2), 2.68 (H-9a), 2.56 (H-9b), 2.54 (H-3'), 2.31/3'N(CH₃)₂/, 1.93 (H-4), 1.79 (H-8), 1.70 (H4'a), 1.47 (H-2"b).

EXAMPLE 21

9-Deoxo-9-dihydro-9a-dimethylamino-8(R)-methyl-10,11,12,13,14,15-hexanor-9a-homoerythromycin A (9a)

To a solution of the substance (8a) (0.3 g, 0.0005 mole) from Example 19 in CHCl₃ (50 ml), 0.05 ml (0.0013 mole) of formic acid (98–100%) and 0.052 ml (0.0007 mole) of formaldehyde (36%) were added. The pH of the reaction mixture was adjusted to 5.2 (with 2% w/v NaOH) and then it was sifted under reflux for 2.5 hours. The isolation of the product was performed as described in Example 16, yielding 0.280 g (89.0%) of TLC homogeneous product (9a).

IR (CHCl₃) cm⁻¹: 3450, 2975, 2940, 1735, 1465, 1375, 1260, 1200, 1165, 1000. ¹H NMR (300 MHz, CDCl₃) δ: 4.641 (H-1"), 4.43 (H-1'), 4.13 (H-3), 4.06 (H-5"), 3.65 (1-OCH₃), 3.64 (H-5), 3.53 (H-5'), 3.30 (H-3"OCH₃), 3.27 (H-2'), 2.97 (H-2), 2.53 ((H-3'), 2.29/3'N(CH₃)₂/, 2.28 (H-2'a), 2.24/9a-N(CH₃)₂/, 2.10 (H-4), 1.96 (H-8), 1.67 (H-7a).

EXAMPLE 22

9-Deoxo-9-dihydro-9a-dimethylamino-8(S)-methyl-10,11,12,13,14,15-hexanor-9a-homoerythromycin A (9b)

To a solution of a substance (8b) (0.6 g, 0.001 mole) from Example 19 in CHCl₃ (50 ml), 0.1 ml (0.0026 mole) of formic acid (98–100%) and 0.104 ml (0.0014 mole) of formaldehyde (36%) were added. The pH of the reaction mixture was adjusted to 5.2 (with 2% w/v NaOH) and then it was stirred under reflux for 2.5 hours. The isolation of the product was performed as described in Example 16, yielding 0.550 g (87.7%) of TLC homogeneous product (9b).

We claim:

1. A compound of the general formula (I)

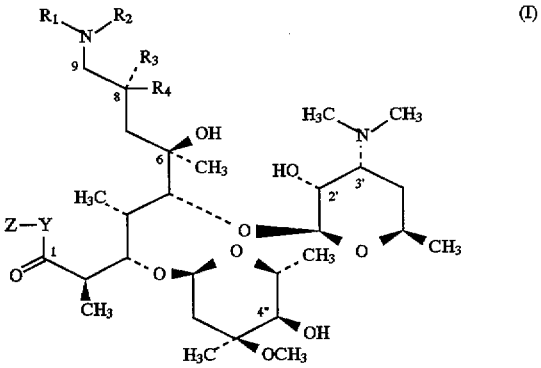

wherein $R_1$ and $R_2$ are the same and represent H or $CH_3$, $R_3$ and $R_4$ are different and represent H or $CH_3$, Y is O or NH, and Z is $CH_3$ or $CH(CH_3)CH(OH)COH(CH_3)CH(OH)C_2H_5$ group, or its pharmaceutically acceptable addition salts with inorganic or organic acids.

2. A compound according to claim 1, wherein $R_1$, $R_2$ and $R_4$ are the same and represent H, $R_3$ is $CH_3$, Y is NH, and Z is $CH(CH_3)CH(OH)COH(CH_3)CH(OH)C_2H_5$.

3. A compound according to claim 1, wherein $R_1$, $R_2$ and $R_3$ are the same and represent H, $R_4$ is $CH_3$, Y is NH, and Z is $CH(CH_3)CH(OH)COH(CH_3)CH(OH)C_2H_5$.

4. A compound according to claim 1, wherein $R_1$, $R_2$ and $R_3$ are the same and represent $CH_3$, $R_4$ is H, Y is NH, and Z is $CH(CH_3)CH(OH)COH(CH_3)CH(OH)C_2H_5$.

5. A compound according to claim 1, wherein $R_1$, $R_2$ and $R_4$ are the same and represent $CH_3$, $R_3$ is H, Y is NH, and Z or $CH(CH_3)CH(OH)COH(CH_3)CH(OH)C_2H_5$.

6. A compound according to claim 1, wherein $R_1$, $R_2$ and $R_4$ are the same and represent H, $R_3$ is $CH_3$, Y is O, and Z is $CH_3$.

7. A compound according to claim 1, wherein $R_1$, $R_2$ and $R_3$ are the same and represent H, $R_4$ is $CH_3$, Y is O, and Z is $CH_3$.

8. A compound according to claim 1, wherein $R_1$, $R_2$ and $R_3$ are the same and represent $CH_3$, $R_4$ is H, Y is O, and Z is $CH_3$.

9. A compound according to claim 1, wherein $R_1$, $R_2$ and $R_4$ are the same and represent $CH_3$, $R_3$ is H, Y is O, and Z is $CH_3$.

10. A compound of the general formula (II)

$$\text{(II)}$$

wherein

X is O or $NOR_7$, wherein $R_7$ is H, acyl or arylsulfonyl group, $R_3$ and $R_4$ are different and represent H or $CH_3$, $R_5$ and $R_6$ are the same or different and represent H or acyl group, Y is O or NH, and Z is $CH_3$, $CH(C_2H_5)COH(CH_3)CH(OR_8)CH(CH_3)NHR_9$ or $CH(CH_3)CH(OR_{10})COH(CH_3)CH(OR_{11})C_2H_5$ group, $R_8$ is H or acyl group, $R_9$ is H, acyl or arylsulfonyl group, and $R_{10}$ and $R_{11}$ are the same and represent H or acyl group, or its pharmaceutically acceptable addition salts with inorganic or organic acids.

11. A compound according to claim 10, wherein X and Y are the same and represent O, $R_3$ is $CH_3$, $R_4$, $R_5$ and $R_6$ are the same and represent H, Z is $CH(C_2H_5)COH(CH_3)CH(OR_8)CH(CH_3)NHR_9$ group, wherein $R_8$ and $R_9$ are the same and represent H.

12. A compound according to claim 10, wherein X and Y are the same and represent O, $R_3$ is $CH_3$, $R_4$ is H, $R_5$ and $R_6$ are the same and represent acetyl group, Z is $CH(C_2H_5)COH(CH_3)CH(OR_8)CH(CH_3)NHR_9$ group, wherein $R_8$ and $R_9$ are the same and represent acetyl group.

13. A compound according to claim 10, wherein X and Y are the same and represent O, $R_3$ is $CH_3$, $R_4$ and $R_5$ are the same and represent H, $R_6$ is acetyl group, and Z is $CH(C_2H_5)COH(CH_3)CH(OR_8)CH(CH_3)NHR_9$ group, wherein $R_8$ and $R_9$ are the same and represent acetyl group.

14. A compound according to claim 10, wherein X and Y are the same and represent O, $R_3$ is $CH_3$, $R_4$, $R_5$ and $R_6$ are the same and represent H, and Z is $CH(C_2H_5)COH(CH_3)CH(OR_8)CH(CH_3)NHR_9$ group, wherein $R_8$ is H and $R_9$ is p-bromobenzoyl group.

15. A compound according to claim 10, wherein X represents $NOR_7$, wherein $R_7$ is H, $R_3$ is $CH_3$, $R_4$, $R_5$ and $R_6$ are the same and represent H, Y is O and Z is $CH(C_2H_5)COH(CH_3)CH(OR_8)CH(CH_3)NHR_9$ group, wherein $R_8$ and $R_9$ are the same and represent H.

16. A compound according to claim 10, wherein X represents $NOR_7$, wherein $R_7$ is acetyl, $R_3$ is $CH_3$, $R_4$ is H, $R_5$ and $R_6$ are the same and represent acetyl group, Y is O and Z is $CH(C_2H_5)COH(CH_3)CH(OR_8)CH(CH_3)NHR_9$ group, wherein $R_8$ and $R_9$ are the same and represent acetyl group.

17. A compound according to claim 10, wherein X represents $NOR_7$, wherein $R_7$ is H, $R_3$ is $CH_3$, $R_4$ and $R_5$ represent H, $R_6$ is acetyl group, Y is O and Z is $CH(C_2H_5)COH(CH_3)CH(OR_8)CH(CH_3)NHR_9$ group, wherein $R_8$ and $R_9$ are the same and represent acetyl group.

18. A compound according to claim 10, wherein X represents $NOR_7$, wherein $R_7$ is tosyl group, $R_3$ is $CH_3$, $R_4$, $R_5$ and $R_6$ are the same and represent H, Y is O and Z is $CH(C_2H_5)COH(CH_3)CH(OR_8)CH(CH_3)NHR_9$ group, wherein $R_8$ is H and $R_9$ is tosyl group.

19. A compound according to claim 10, wherein X represents $NOR_7$, wherein $R_7$ is H, $R_3$ is $CH_3$, $R_4$, $R_5$ and $R_6$ are the same and represent H, Y is O and Z is $CH(C_2H_5)COH(CH_3)CH(OR_8)CH(CH_3)NHR_9$ group, wherein $R_8$ is H and $R_9$ is tosyl group.

20. A compound according to claim 10, wherein X represents $NOR_7$, wherein $R_7$ is H, $R_3$ is H, $R_4$ is $CH_3$, Y is O and Z is $CH(C_2H_5)COH(CH_3)CH(OR_8)CH(CH_3)NHR_9$ group, wherein $R_8$ and $R_9$ are the same and represent H.

21. A compound according to claim 10, wherein X represents $NOR_7$, wherein $R_7$ is H, $R_3$ is $CH_3$, $R_4$, $R_5$ and $R_6$ are the same and represent H, Y is NH and Z is $CH(CH_3)CH(OR_{10})COH(CH_3)CH(OR_{11})C_2H_5$ group, wherein $R_{10}$ and $R_{11}$ are the same and represent H.

22. A compound according to claim 10, wherein X represents $NOR_7$, wherein $R_7$ is acetyl, $R_3$ is $CH_3$, $R_4$ is H, $R_5$ and $R_6$ are the same and represent acetyl, Y is NH and Z is $CH(CH_3)CH(OR_{10})COH(CH_3)CH(OR_{11})C_2H_5$ group, wherein $R_{10}$ and $R_{11}$ are the same and represent acetyl.

23. A compound according to claim 10, wherein X represents $NOR_7$, wherein $R_7$ is acetyl, $R_3$ is $CH_3$, $R_4$ and $R_5$ are the same and represent H, $R_6$ is acetyl group, Y is NH and Z is $CH(CH_3)CH(OR_{10})COH(CH_3)CH(OR_{11})C_2H_5$ group, wherein $R_{10}$ and $R_{11}$ are the same and represent acetyl.

24. A compound according to claim 10, wherein X represents $NOR_7$, wherein $R_7$ is H, $R_3$ is $CH_3$, $R_4$ and $R_5$ are the same and represent H, $R_6$ is acetyl group, Y is NH and Z is $CH(CH_3)CH(OR_{10})COH(CH_3)CH(OR_{11})C_2H_5$ group, wherein $R_{10}$ and $R_{11}$ are the same and represent acetyl.

25. A compound according to claim 10, wherein X represents $NOR_7$, wherein $R_7$ is tosyl, $R_3$ is $CH_3$, $R_4$, $R_5$ and $R_6$ are the same and represent H, Y is NH and Z is $CH(CH_3)CH(OR_{10})COH(CH_3)CH(OR_{11})C_2H_5$ group, wherein $R_{10}$ and $R_{11}$ are the same and represent H.

26. A compound according to claim 10, wherein X represents $NOR_7$, wherein $R_7$ is H, $R_3$, $R_5$, and $R_6$ are the same and represent H, $R_4$ is $CH_3$, Y is NH and Z is $CH(CH_3)CH(OR_{10})COH(CH_3)CH(OR_{11})C_2H_5$ group, wherein $R_{10}$ and $R_{11}$ are the same and represent H.

27. A compound according to claim 10, wherein X represents $NOR_7$, wherein $R_7$ is H, $R_3$ is $CH_3$, $R_4$, $R_5$ and $R_6$ and $R_6$ are the same and represent H, Y is O and Z is $CH_3$.

28. A compound according to claim 10, wherein X represents $NOR_7$, wherein $R_7$ is H, $R_3$, $R_5$, and $R_6$ are the same and represent H, $R_4$ is $CH_3$, Y is O and Z is $CH_3$.

29. A process for the preparation of compounds of the general formula (I)

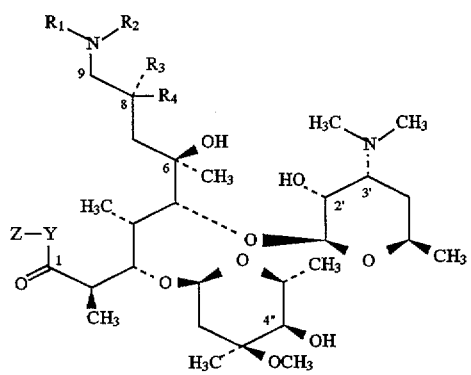

(I)

wherein $R_1$ and $R_2$ are the same and represent H or $CH_3$, $R_3$ and $R_4$ are different and represent H or $CH_3$, Y is O or NH, and Z is $CH_3$ or $CH(CH_3)CH(OH)COH(CH_3)CH(OH)C_2H_5$ group, or their pharmaceutically acceptable addition salts with inorganic or organic acids, characterized in that erythromycin A imino ether of formula (III),

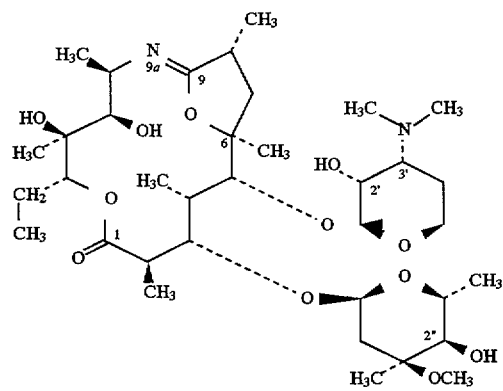

(III)

is subjected

A) to the action of acetic acid under the conditions of the hydrolysis of the imino group and then optionally to N- or O-acylation or both with acid anhydrides or chlorides and then optionally to methanolysis, or B) to the reaction with hydroxylamine hydrochloride in the presence of appropriate inorganic or organic bases, in a solvent inert to the reaction, in one or two reaction steps and then optionally B1) to the action of appropriate inorganic or organic acids under the conditions of the hydrolysis of the hydroxyimino group and then optionally to N- or O-acylation or both with acid anhydrides or chlorides and then optionally B3) to the action of appropriate organic or inorganic basis under the conditions of internal amine acylation and then optionally to N- or O-acylation or both with acid anhydrides or chlorides and then optionally to methanolysis, yielding compounds of the general formula (II),

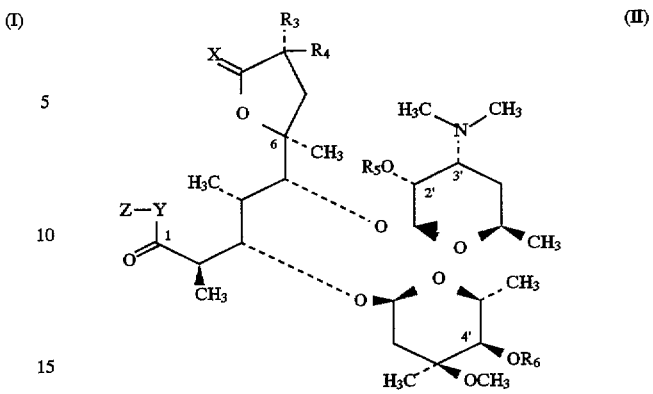

(II)

wherein

X is O or $NOR_7$, wherein $R_7$ is H, acyl or arylsulfonyl group, $R_3$ and $R_4$ are different and represent H or $CH_3$, $R_5$ and $R_6$ are the same or different and represent H or acyl group, Y is O or NH, and Z is $CH_3$, $CH(C_2H_5)COH(CH_3)CH(OR_8)CH(CH_3)NH_9$ or $CH(CH_3)CH(OR_{10})COH(CH_3)CH(OR_{11})C_2H_5$ group, $R_8$ is H or acyl group, $R_9$ is H, acyl or arylsulfonyl group, and $R_{10}$ and $R_{11}$ are the same and represent H or acyl group, and their pharmaceutically acceptable addition salts with inorganic or organic acids, which optionally are subjected to a catalytic reduction in a solvent inert to the reaction, and then optionally to reductive N-alkylation with appropriate alkylation agents in the presence of appropriate reductive agents, yielding compounds of the general formula (I), wherein $R_1$, $R_2$, $R_3$, $R_4$, Y and Z have the abovementioned meanings.

30. A process according to claim 29, characterized in that erythromycin A imino ether of formula (III) is subjected to the action of acetic acid under the conditions of hydrolysis of imino group at room temperature within 3 days.

31. A process according to claim 29, characterized in that the reaction of erythromycin A imino ether of formula (III) with hydroxylamine hydrochloride is performed at a temperature from 25° to 70° C.

32. A process according to claim 31, characterized in that the appropriate inorganic or organic bases are sodium carbonate, potassium carbonate or pyridine.

33. A process according to claim 31, characterized in that the solvent inert to the reaction is methanol or pyridine.

34. A process according to claim 29, characterized in that N- and/or O-acylation of a compound of the general formula (II)

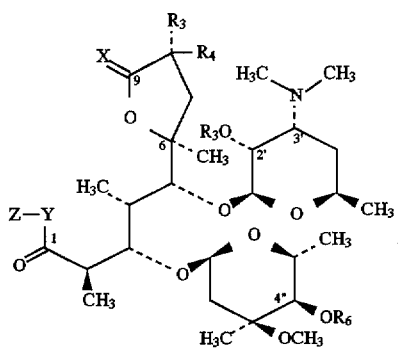
(II)

wherein

X is O or NOR$_7$, wherein R$_7$ is H,

R$_3$ is CH$_3$, and R$_4$ is H or

R$_3$ is H and R$_4$ is CH$_3$,

R$_5$ and R$_6$ are the same and represent H,

Y is O or NH, and

Z is, CH(C$_2$H$_5$)COH(CH$_3$)CH(OR$_8$)CH(CH$_3$)NHR$_9$ or CH(CH$_3$)CH(OR$_{10}$)COH(CH$_3$)CH(OR$_{11}$)C$_2$H$_5$ group, wherein R$_8$, R$_9$, R$_{10}$ and R$_{11}$ are the same and represent H, is performed with acetic acid anhydride in pyridine at room temperature, or with tosylchloride in acetone at a temperature from 0° to 5° C., or with 4-bromobenzoyl chloride in diethylether at a temperature from 0° to 5° C.

35. A process according to claim 34, characterized in that a compound of the general formula (II),
wherein X is O or NOR$_7$, wherein R$_7$ is acetyl group, R$_3$ is CH$_3$, and R$_4$ is H or R$_3$ is H and R$_4$ is CH$_3$, R$_5$ and R$_6$ are the same and represent acetyl group, Y is O or NH, and Z is, CH(C$_2$H$_5$)COH(CH$_3$)CH(OR$_8$)CH(CH$_3$)NHR$_9$ or CH(CH$_3$)CH(OR$_{10}$)COH(CH$_3$)CH(OR$_{11}$)C$_2$H$_5$ group, wherein R$_8$, R$_9$, R$_{10}$ and R$_{11}$ are the same and represent acetyl group, is subjected optionally to methanolysis yielding a compound of the general formula (II),
wherein X is O or NOR$_7$, wherein R$_7$ is H or acetyl group, R$_3$ is CH$_3$, and R$_4$ is H or R$_3$ is H and R$_4$ is CH$_3$, R$_5$ is H, R$_6$ is acetyl group, Y is O or NH, and Z is, CH(C$_2$H$_5$)COH(CH$_3$)CH(OR$_8$)CH(CH$_3$)NHR$_9$ or CH(CH$_3$)CH(OR$_{10}$)COH(CH$_3$)CH(OR$_{11}$)C$_2$H$_5$ group, wherein R$_8$, R$_9$, R$_{10}$ and R$_{11}$ are the same and represent acetyl group.

36. A process according to claim 29, characterized in that the appropriate inorganic or organic acids under the conditions of hydrolysis of hydroxyimino group are HCl or CH$_3$COOH.

37. A process according to claim 29, characterized in that the appropriate inorganic or organic bases under the conditions of internal amine acylation are ammonium hydroxide, sodium hydroxide, potassium hydroxide or triethylamine.

38. A process according to claim 29, characterized in that the catalytic reduction in a solvent inert to the reaction is performed in the presence of noble metals or their oxides as catalysts at room temperature and at a hydrogen pressure from $5 \times 10^5$ to $7 \times 10^6$ Pa.

39. A process according to claim 38, characterized in that the said catalyst is platinum (IV) oxide.

40. A process according to claim 38, characterized in that the solvent inert to the reaction is glacial acetic acid.

41. A process according to claim 29, characterized in that the reductive N-alkylation of compound of the general formula (I),
wherein R$_1$ and R$_2$ are the same and represent H, R$_3$ is CH$_3$, and R$_4$ is H or R$_3$ is H and R$_4$ is CH$_3$, Y is NH, and Z is, CH$_3$ or CH(CH$_3$)CH(OH)COH(CH$_3$)CH(OH)C$_2$H$_5$ group, or their pharmaceutically acceptable addition salts with inorganic or organic acids, is performed with appropriate alkylation agents in the presence of appropriate reductive agents in a solvent inert to the reaction at reflux temperature, yielding compounds of the general formula (I),
wherein R$_1$ and R$_2$ are the same and represent CH$_3$, R$_3$ is CH$_3$, and R$_4$ is H or R$_3$ is H and R$_4$ is CH$_3$, Y is NH, and Z is, CH$_3$ or CH(CH$_3$)CH(OH)COH(CH$_3$)CH(OH)C$_2$H$_5$ group, or their pharmaceutically acceptable addition salts with inorganic or organic acids.

42. A process according to claim 41, characterized in that an appropriate alkylation agent for the reductive alkylation process is an aldehyde.

43. A process according to claim 42, characterized in that an appropriate aldehyde is formaldehyde.

44. A process according to claim 41, characterized in that an appropriate reductive agent is formic acid.

45. A process according to claim 41, characterized in that a solvent inert to the reaction is chloroform.

* * * * *